US009862886B2

(12) United States Patent
Jang et al.

(10) Patent No.: US 9,862,886 B2
(45) Date of Patent: Jan. 9, 2018

(54) COMPOUND, LIQUID CRYSTAL COMPOSITION INCLUDING THE SAME, AND LIQUID CRYSTAL DISPLAY DEVICE INCLUDING THE SAME

(71) Applicant: Samsung Display Co., Ltd., Yongin-si, Gyeonggi-do (KR)

(72) Inventors: Hye Lim Jang, Hwaseong-si (KR); Beom-Soo Shin, Hwaseong-si (KR); Si Heun Kim, Hwaseong-si (KR); Keun Chan Oh, Cheonan-si (KR); Bong Hee Kim, Hwaseong-si (KR); Sun Hee Lee, Anyang-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/184,212

(22) Filed: Jun. 16, 2016

(65) Prior Publication Data
US 2016/0369167 A1 Dec. 22, 2016

(30) Foreign Application Priority Data
Jun. 22, 2015 (KR) ........................ 10-2015-0088642

(51) Int. Cl.
*G02F 1/1333* (2006.01)
*C09K 19/34* (2006.01)
(Continued)

(52) U.S. Cl.
CPC ........ *C09K 19/3402* (2013.01); *C07C 43/225* (2013.01); *C07D 309/06* (2013.01);
(Continued)

(58) Field of Classification Search
CPC .... C09K 19/3402; C09K 19/04; C09K 19/20; C09K 19/3066; C09K 19/12;
(Continued)

(56) References Cited

U.S. PATENT DOCUMENTS 6,677,003 B2   1/2004   Lussem et al.
6,692,796 B2   2/2004   Ichinose et al.

FOREIGN PATENT DOCUMENTS

CN   104610983 A   5/2015
EP   1199346   4/2002
(Continued)

OTHER PUBLICATIONS

Extended European Search Report dated Nov. 16, 2016, of the corresponding European Patent Application No. 16175763.8 w/English Translation.

*Primary Examiner* — Geraldina Visconti
(74) *Attorney, Agent, or Firm* — Cantor Colburn LLP

(57) ABSTRACT

An exemplary embodiment of the present invention provides a compound represented by Chemical Formula 1:

[Chemical Formula 1]

wherein, in Chemical Formula 1, n is 0, 1, or 2, and a substituent represented by X is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms; ($R_1$) is hydrogen or a C1 to C15 alkyl, at least one $CH_2$ group being independently replaced with —C≡C—, —$CF_2$O—, —CH=CH—, —O—, —CO—O—, —O—CO—, or —O—CO—O— in a way that oxygen atoms are directly connected to each other, and 1 to 3 hydrogen atoms of the C1 to C15 alkyl being replaced with halogen; (F) indicates that a fluoro is optionally substituted in place of a hydrogen, and
each of A1 and A2 is independently (Continued)

-continued

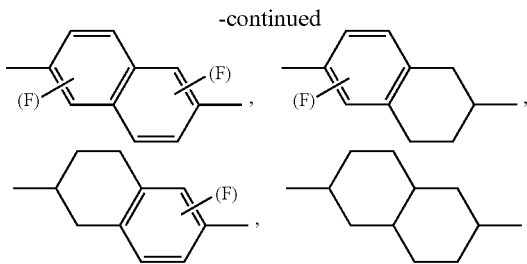

24 Claims, 4 Drawing Sheets

(51) Int. Cl.
| | |
|---|---|
| C09K 19/04 | (2006.01) |
| C09K 19/20 | (2006.01) |
| C09K 19/30 | (2006.01) |
| C07C 43/225 | (2006.01) |
| C07D 309/06 | (2006.01) |
| C07D 319/06 | (2006.01) |
| G02F 1/1343 | (2006.01) |
| G02F 1/1368 | (2006.01) |
| C09K 19/12 | (2006.01) |

(52) U.S. Cl.
CPC ............ *C07D 319/06* (2013.01); *C09K 19/04* (2013.01); *C09K 19/12* (2013.01); *C09K 19/20* (2013.01); *C09K 19/3066* (2013.01); *G02F 1/1368* (2013.01); *G02F 1/133345* (2013.01); *G02F 1/134309* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/3016* (2013.01); *C09K 2019/3019* (2013.01); *C09K 2019/3422* (2013.01)

(58) Field of Classification Search
CPC ...... C09K 2019/0466; C09K 2019/123; C09K 2019/3004; C09K 2019/301; C09K 2019/3016; C09K 2019/3019; C09K 2019/3422; C09K 2019/122; G02F 1/1333; G02F 1/133345; G02F 1/134309; G02F 1/1368; C07C 43/225; C07D 309/06; C07D 319/06
USPC ........................................ 252/299.6; 428/1.1
See application file for complete search history.

(56) References Cited

FOREIGN PATENT DOCUMENTS

| JP | 2004149774 | | 5/2004 |
|---|---|---|---|
| KR | 101095695 | | 12/2011 |
| KR | 101355763 | | 1/2014 |
| KR | 101374694 | | 3/2014 |
| KR | 101447764 | | 9/2014 |
| WO | 2005019377 | A1 | 3/2005 |
| WO | 2005019378 | A1 | 3/2005 |

COMPOUND, LIQUID CRYSTAL COMPOSITION INCLUDING THE SAME, AND LIQUID CRYSTAL DISPLAY DEVICE INCLUDING THE SAME

This application claims priority to and the benefit of Korean Patent Application No. 10-2015-0088642, filed on Jun. 22, 2015, the content of which in its entirety is herein incorporated by reference.

BACKGROUND

(a) Field

The present invention relates to a compound, a liquid crystal composition including the compound, and a liquid crystal display including the liquid crystal composition.

(b) Description of the Related Art

Liquid crystal displays are widely used as one of flat panel displays. The liquid crystal display determines a direction of the liquid crystal molecules within the liquid crystal layer and controls transmittance of light passing through the liquid crystal layer by applying a voltage to the field generating electrodes to generate an electric field in the liquid crystal layer.

The liquid crystal enables the liquid crystal display to achieve a desired image by controlling the transmittance of light. In particular, with different uses of liquid crystal displays, various characteristics of the liquid crystal are optimized, such as low-voltage driving, a high voltage holding ratio (VHR), a wide viewing angle, a wide operation temperature range, and high-speed response.

In order to obtain high-speed response characteristics for a liquid crystal display, studies for improving the physical properties of the liquid crystal composition, such as rotational viscosity, refractive index, and elastic coefficient, are in progress.

The above information disclosed in this Background section is only for enhancement of understanding of the background of the invention and therefore it may contain information that does not form the prior art that is already known in this country to a person of ordinary skill in the art.

SUMMARY

Disclosed herein are a liquid crystal composition and a display device including the same, capable of realizing high speed response characteristics and low temperature stability.

An exemplary embodiment provides a compound represented by Chemical Formula 1:

[Chemical Formula 1]

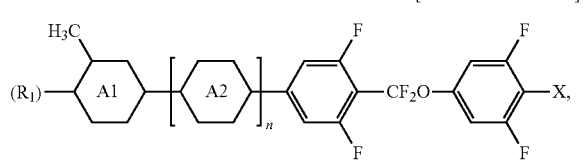

In Chemical Formula 1, n is 0, 1, or 2, and a substituent represented by X is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms, ($R_1$) is hydrogen or a C1 to C15 alkyl, in which at least one $CH_2$ group is independently substituted with —C≡C—, —$CF_2$O—, —CH=CH—, —O—, —CO—O—, —O—CO—, or —O—CO—O— in a way that oxygen atoms are directly connected to each other, and 1 to 3 hydrogen atoms are substituted with halogen, (F) indicates that a fluoro may be substituted or unsubstituted, and each of

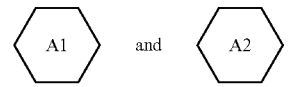

are independently

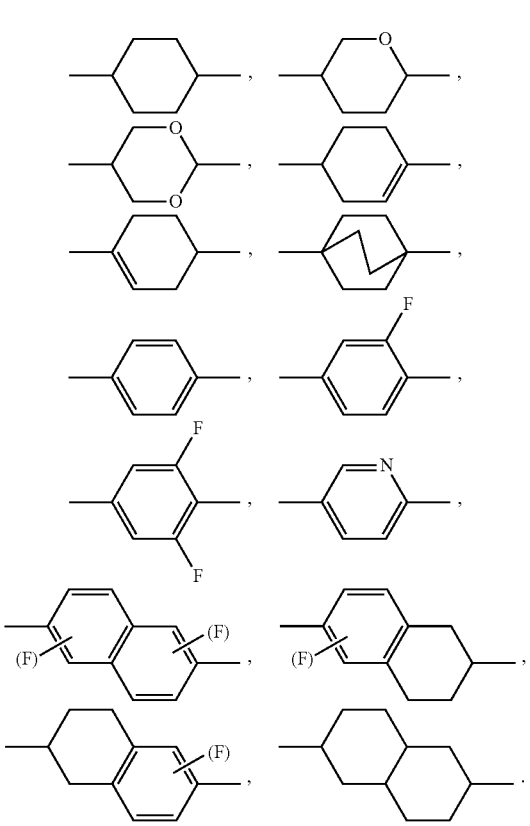

In an exemplary embodiment, the compound represented by Chemical Formula 1 may include one or more compound represented by Chemical Formula 1-1 to Chemical Formula 1-14.

(1-1)

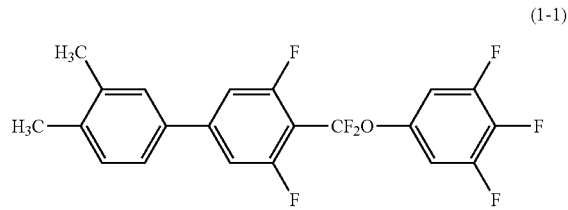

-continued (1-2) 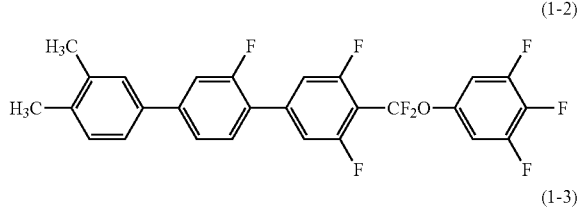

(1-3) 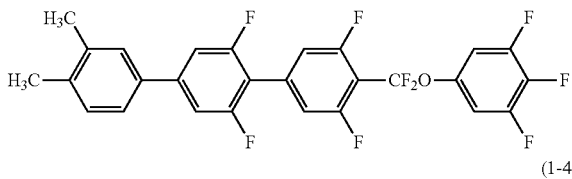

(1-4) 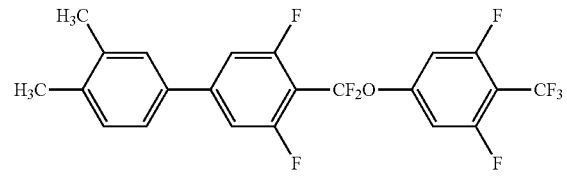

(1-5) 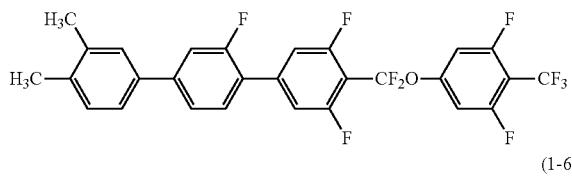

(1-6) 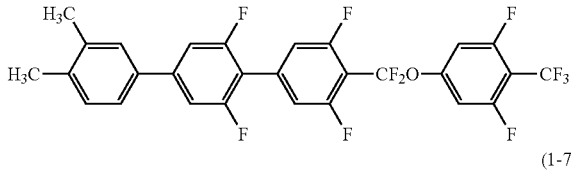

(1-7) 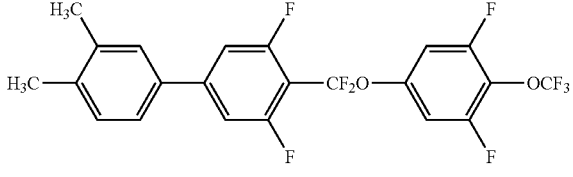

(1-8) 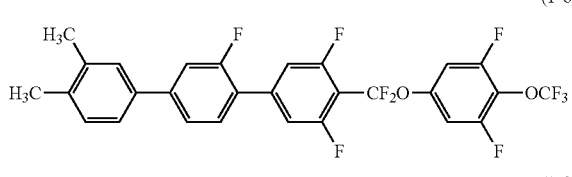

(1-9) 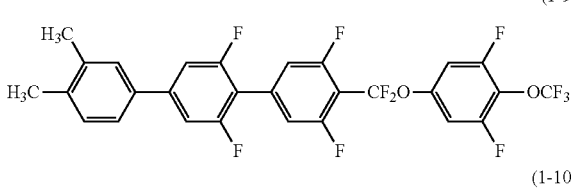

(1-10) 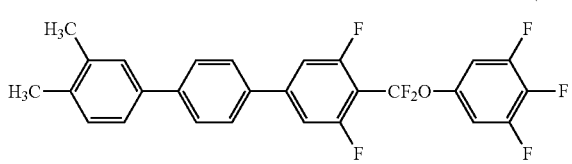

(1-11) 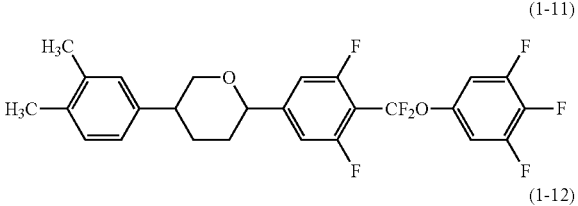

(1-12) 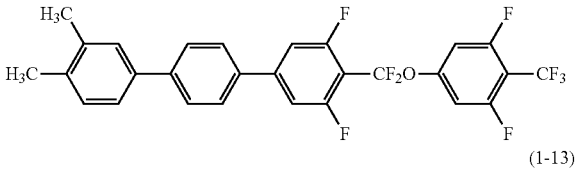

(1-13) 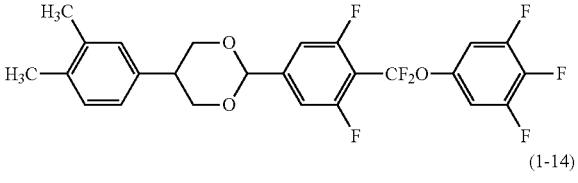

(1-14) 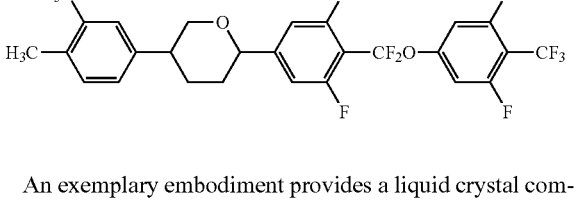

An exemplary embodiment provides a liquid crystal composition including a compound represented by Chemical Formula 1:

[Chemical Formula 1]

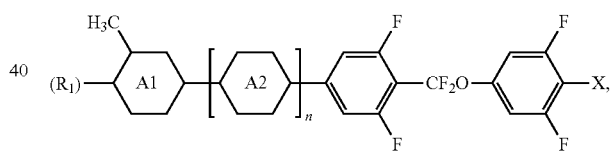

wherein, in Chemical Formula 1, n is 0, 1, or 2, and a substituent represented by X is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms, ($R_1$) is hydrogen or a C1 to C15 alkyl, in which at least one $CH_2$ group is independently substituted with —C≡C—, —$CF_2$O—, —CH=CH—, —O—, —CO—O—, —O—CO—, or —O—CO—O— in a way that oxygen atoms are directly connected to each other, and 1 to 3 hydrogen atoms are substituted with halogen, (F) indicates that a fluoro may be substituted or unsubstituted, and each of

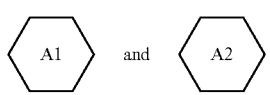

is independently
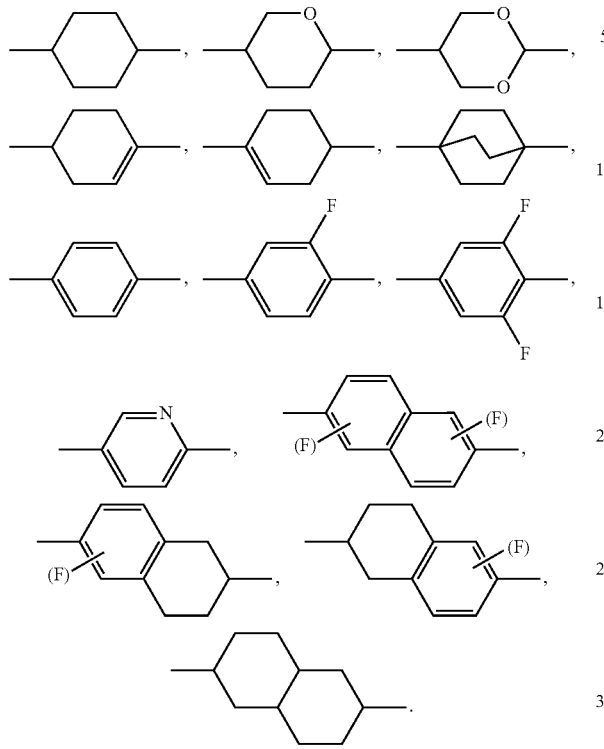
In an exemplary embodiment, a liquid crystal composition including the compound represented by Chemical Formula 1 may include one of more compounds represented by Chemical Formula 1-1 to Chemical Formula 1-14.
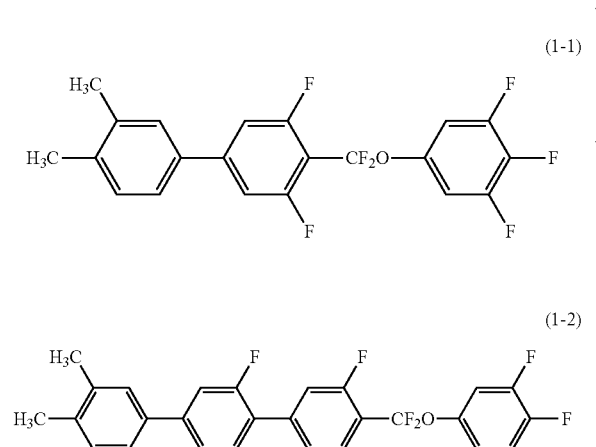
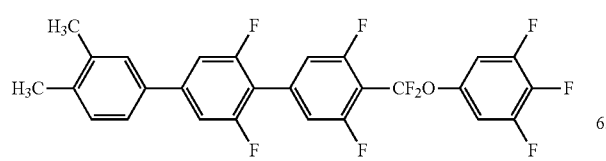
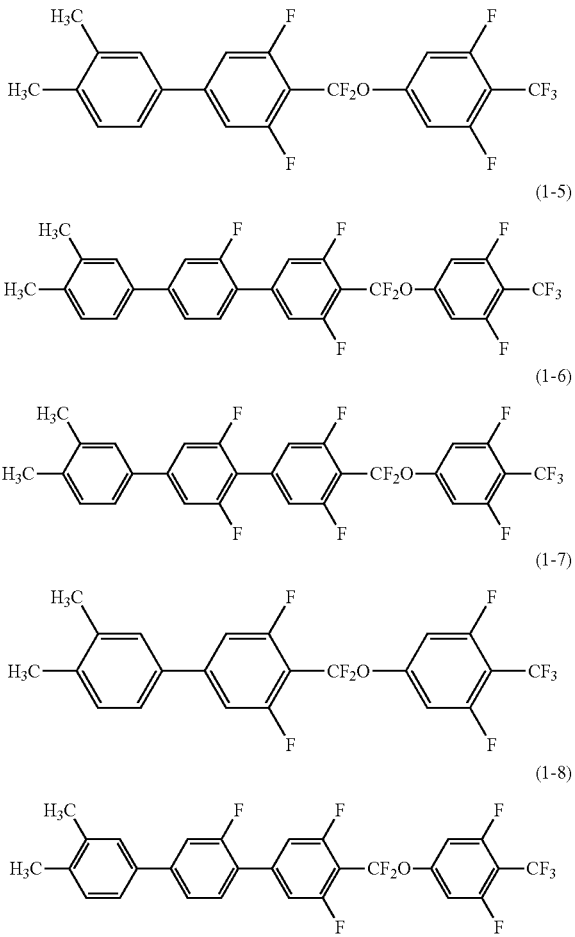
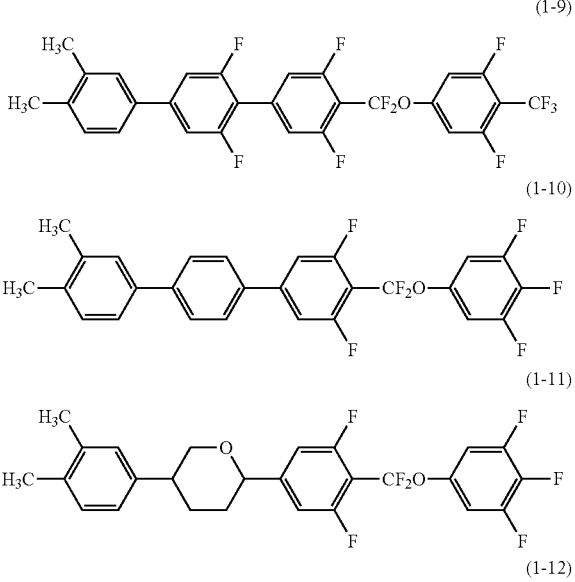
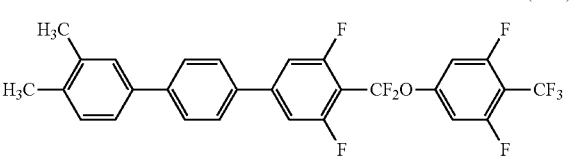

(1-13)

[Structure: H3C, H3C-phenyl-dioxane-phenyl(F,F)-CF2O-phenyl(F,F)-F]

(1-14)

[Structure: H3C, H3C-phenyl-tetrahydropyran-phenyl(F,F)-CF2O-phenyl(F,F)-CF3]

In an exemplary embodiment, the content of the compound represented by Chemical Formula 1 may be in a range of about 1 wt % to about 30 wt % of the total weight of the liquid crystal composition.

In an exemplary embodiment, the liquid crystal composition may further include one or more of the compound represented by Chemical Formula 2.

[Chemical Formula 2]

$R_1$—[cyclohexyl]—[cyclohexyl]—$R_2$,

In Chemical Formula 2, $R_1$ and $R_2$ may independently indicate C1 to C12 alkyl, C1 to C12 alkoxy, or C2 to C12 alkenyl.

In an exemplary embodiment, a content of the compound represented by Chemical Formula 2 may be in a range of about 5 wt % to about 60 wt % of the total liquid crystal composition.

In an exemplary embodiment, the liquid crystal composition may further include one or more of the compound represented by Chemical Formula 3:

[Chemical Formula 3]

$R_3$—A1—A2—A3—$R_4$, wherein each of

A1, A2, A3 may independently be

[ring structures: cyclohexyl, tetrahydropyran, dioxane, cyclohexenyl, cyclohexene, bicyclic, phenyl, fluorophenyl, difluorophenyl, pyridyl, naphthyl(F), tetrahydronaphthyl(F), tetrahydronaphthyl(F), decahydronaphthyl]

and (F) indicates that a fluoro is optionally substituted in place of a hydrogen, $R_3$ and $R_4$ independently indicate C1 to C12 alkyl, C1 to C12 alkoxy, or C2 to C12 alkenyl.

In an exemplary embodiment, a content of the compound represented by Chemical Formula 3 may be in a range of about 1 wt % to about 40 wt % of the total weight of the liquid crystal composition.

In an exemplary embodiment, the liquid crystal composition may further include one or more of the compound represented by Chemical Formula 4:

[Chemical Formula 4]

$R_5$—A4—A5—[phenyl(F, F)]—F, wherein each of

A4, A5 may independently be

[ring structures: cyclohexyl, tetrahydropyran, dioxane, cyclohexenyl]

-continued

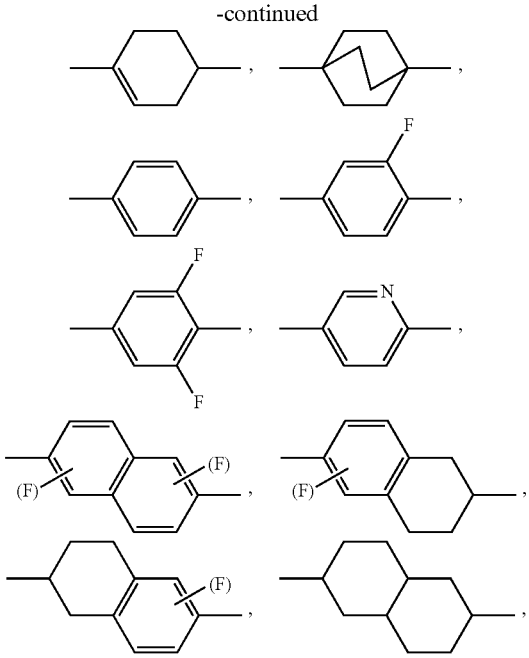

wherein R₅ may indicate C1 to C12 alkyl, C1 to C12 alkoxy, or C2 to C12 alkenyl, and (F) may indicate that a fluoro is substituted or unsubstituted.

In an exemplary embodiment, a content of the compound represented by Chemical Formula 4 may be in a range of about 1 wt % to about 40 wt %.

The liquid crystal composition further includes one or more of the compound represented by Chemical Formula 5:

[Chemical Formula 5]

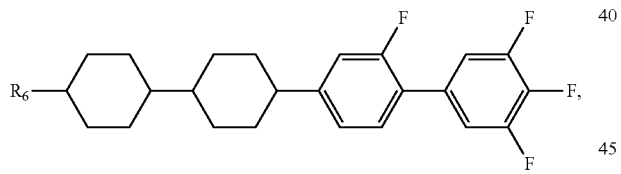

and

R₆ may indicate C1 to C12 alkyl, C1 to C12 alkoxy, or C2 to C12 alkenyl.

In an exemplary embodiment, a content of the compound represented by Chemical Formula 5 may be in a range of about 1 wt % to about 15 wt % of the total weight of the liquid crystal composition.

An exemplary embodiment provides a liquid crystal display including: a first insulation substrate; a thin film transistor disposed on the first insulation substrate; a first electrode connected to the thin film transistor; a second electrode disposed on the first insulation substrate while being insulated from the first electrode; a second insulation substrate configured to face the first insulation substrate; and a liquid crystal layer disposed between the first insulation substrate and the second insulation substrate, wherein the liquid crystal layer includes a liquid crystal composition including a compound represented by Chemical Formula 1:

[Chemical Formula 1]

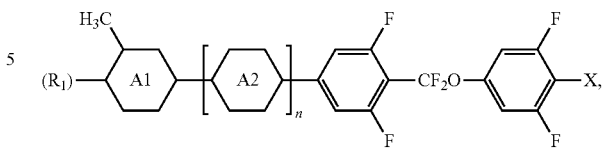

wherein, in Chemical Formula 1, n is 0, 1, or 2, and a substituent represented by X is F, Cl, CF₃, CF₂CF₃, CHF₂, CH₂F, OCF₃, CN, NCS, or a C1 to C5 alkyl including 1 to 3 fluoro substituents and a CH₂ group independently substituted with one or more oxygen atoms;

(R₁) is hydrogen or a C1 to C15 alkyl, in which at least one CH₂ group is independently substituted with —C≡C—, —CF₂O—, —CH=CH—, —O—, —CO—O—, —O—CO—, or —O—CO—O— in a way that oxygen atoms are directly connected to each other, and 1 to 3 hydrogen atoms are substituted with a halogen;

(F) indicates that a fluoro may be substituted or unsubstituted; and each of

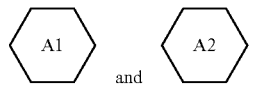

may independently be

In an exemplary embodiment, the compound represented by Chemical Formula 1 may include one or more compounds represented by Chemical Formula 1-1 to Chemical Formula 1-14.

(1-1)
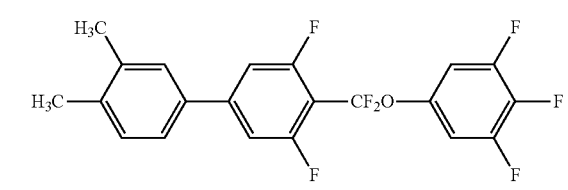

(1-2)
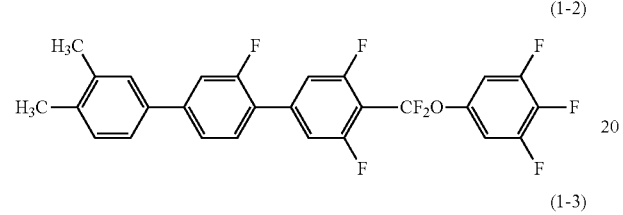

(1-3)
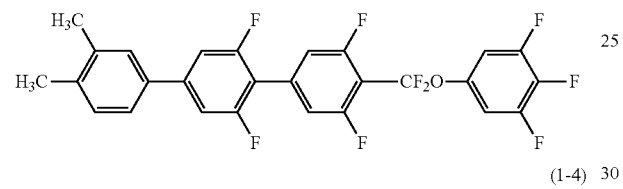

(1-4)
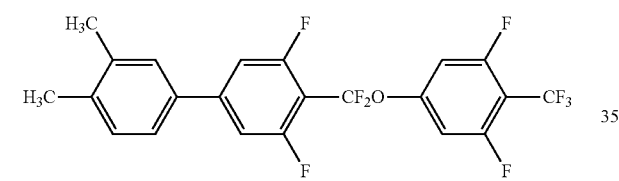

(1-5)
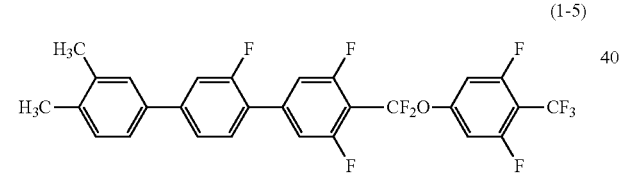

(1-6)
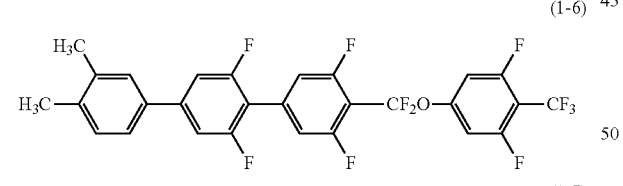

(1-7)
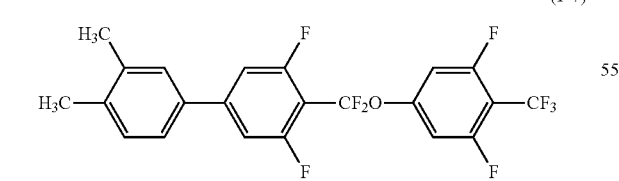

(1-8)
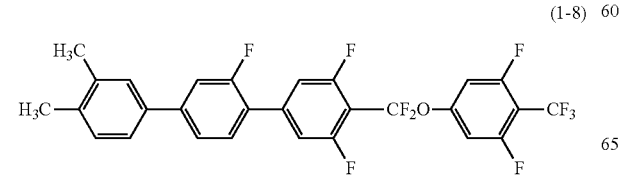

(1-9)
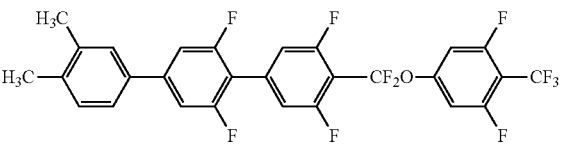

(1-10)
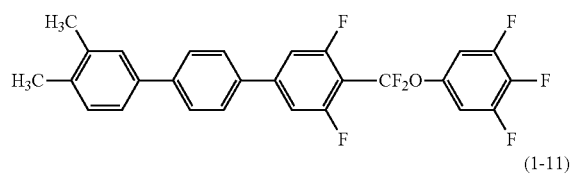

(1-11)
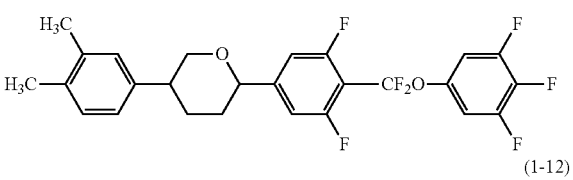

(1-12)
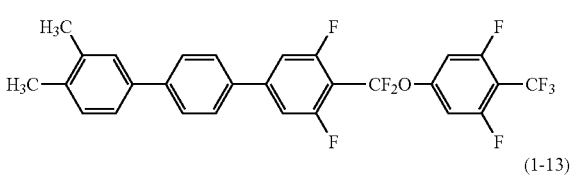

(1-13)
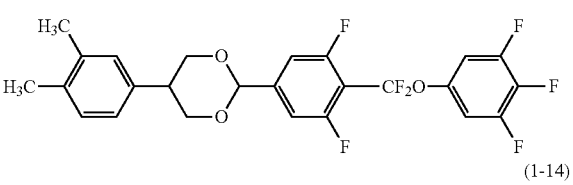

(1-14)
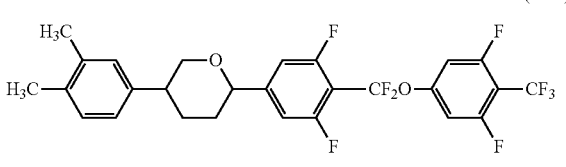

In an exemplary embodiment, a content of the compound represented by Chemical Formula 1 may be in a range of about 1 wt % to about 30 wt % of the total weight of the liquid crystal composition.

In an exemplary embodiment, the liquid crystal composition may include one or more of the compound represented by Chemical Formula 2.

[Chemical Formula 2]

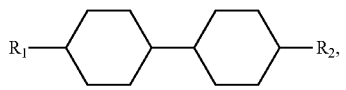

In Chemical Formula 2, $R_1$ and $R_2$ may independently indicate C1 to C12 alkyl, C1 to C12 alkoxy, or C2 to C12 alkenyl.

In an exemplary embodiment, a content of the compound represented by Chemical Formula 2 may be in a range of about 5 wt % to about 60 wt % of the total weight of the liquid crystal composition.

In an exemplary embodiment, the liquid crystal composition may include one or more of the compound represented by Chemical Formula 3:

[Chemical Formula 3]

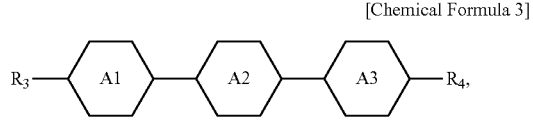

wherein each of

may independently be

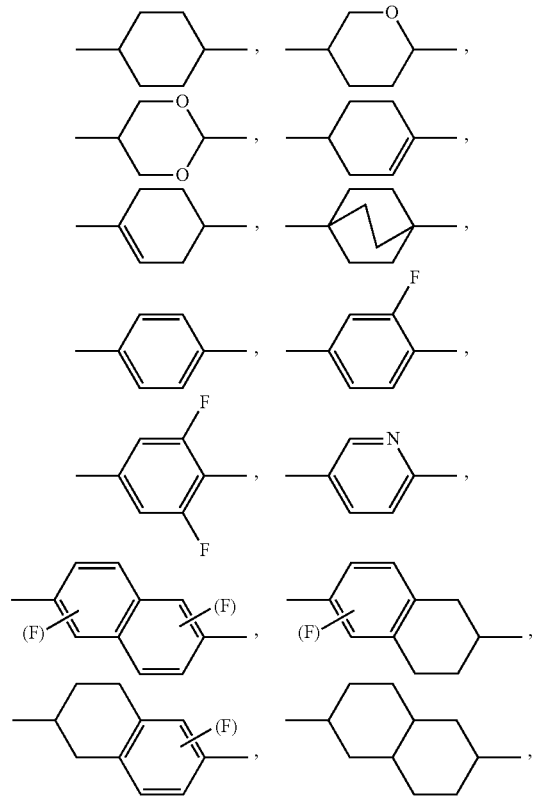

wherein (F) indicates that a fluoro is optionally substituted in place of a hydrogen, and $R_3$ and $R_4$ may independently indicate C1 to C12 alkyl, C1 to C12 alkoxy, or C2 to C12 alkenyl.

In an exemplary embodiment, a content of the compound represented by Chemical Formula 3 may be in a range of about 1 wt % to about 40 wt % of the total weight of the liquid crystal composition.

In an exemplary embodiment, the liquid crystal composition may include one or more of the compound represented by Chemical Formula 4:

[Chemical Formula 4]

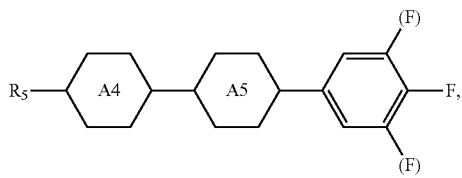

wherein each of

may independently be

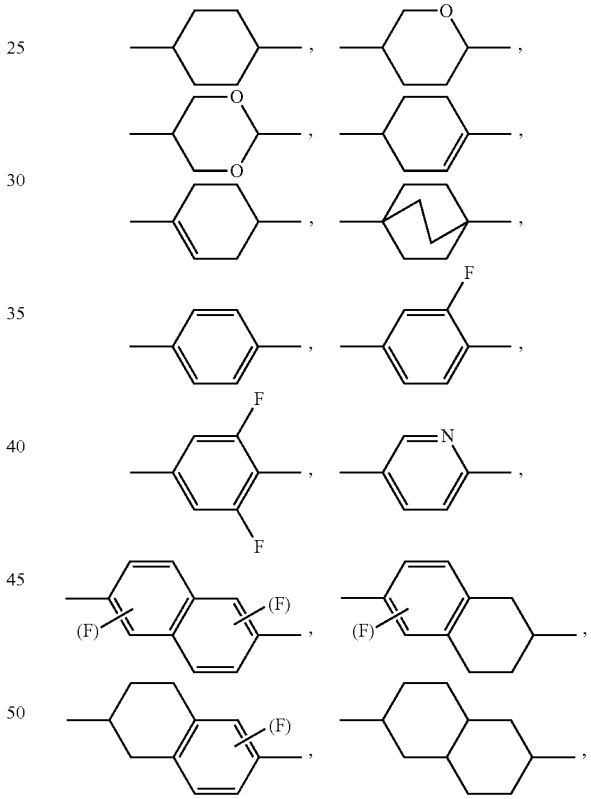

$R_5$ may indicate C1 to C12 alkyl, C1 to C12 alkoxy, or C2 to C12 alkenyl, and (F) may indicate that a fluoro is substituted or unsubstituted.

In an exemplary embodiment, a content of the compound represented by Chemical Formula 4 may be in a range of about 1 wt % to about 40 wt % of the total weight of the liquid crystal composition.

In an exemplary embodiment, the liquid crystal composition may include one or more compound represented by Chemical Formula 5:

[Chemical Formula 5]

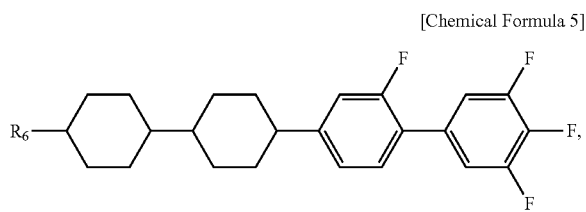

and

R₆ may indicate C1 to C12 alkyl, C1 to C12 alkoxy, or C2 to C12 alkenyl.

In an exemplary embodiment, content of the compound represented by Chemical Formula 5 may be in a range of about 1 wt % to about 15 wt % of the total weight of the liquid crystal composition.

According to the exemplary embodiments disclosed herein, it is possible to improve the performance of a liquid crystal display by manufacturing the liquid crystal display using a liquid crystal composition including the exemplary compound.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

Figure 1:
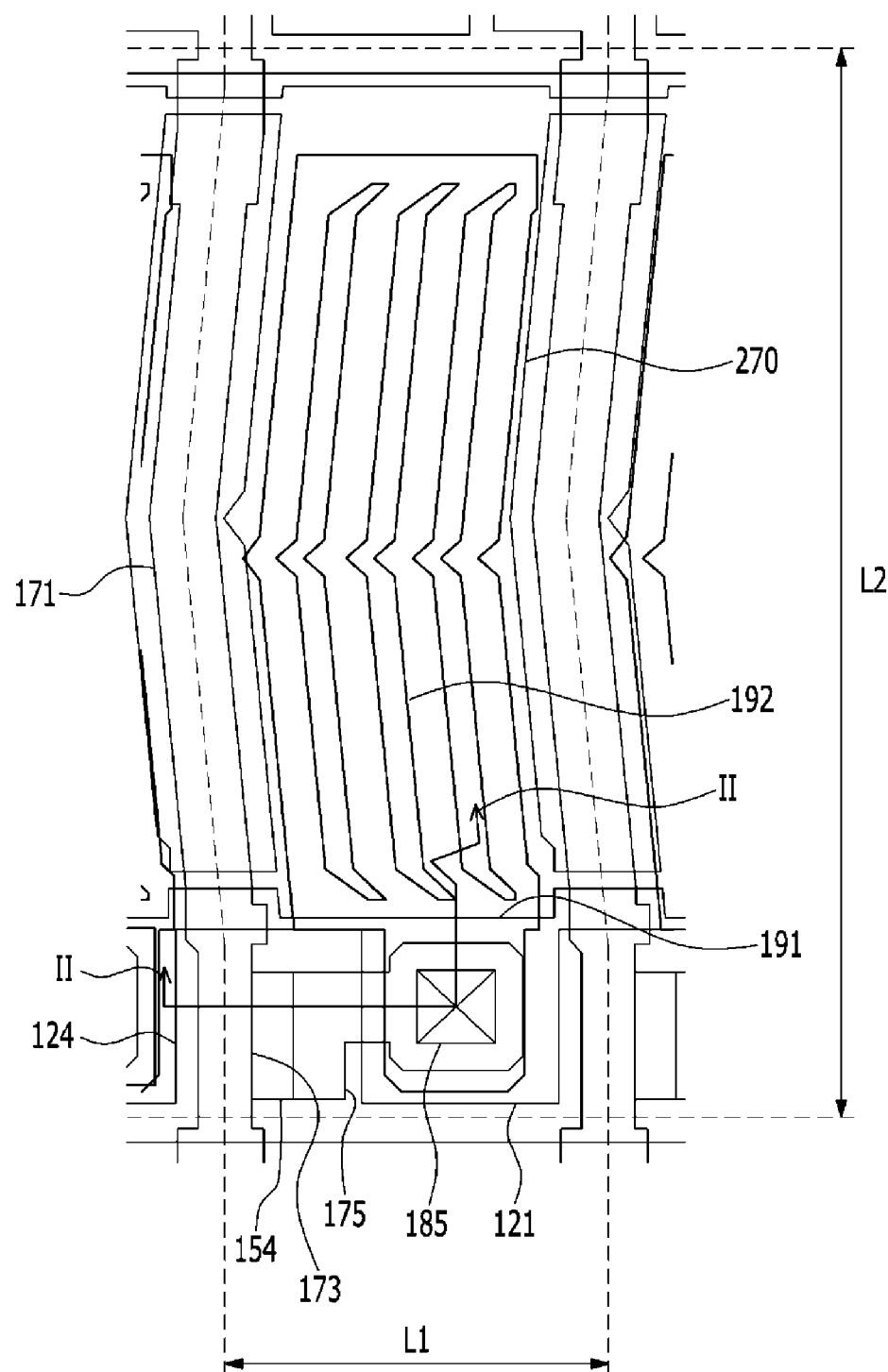
FIG. 1 is a plan view illustrating a portion of a pixel area of an exemplary embodiment of a display device.

The present invention will now be described more fully hereinafter with reference to the accompanying drawings, in which exemplary embodiments are shown. As those skilled in the art would realize, the described embodiments may be modified in various different ways, all without departing from the spirit or scope of the present invention.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

An "alkyl" group as used herein means a C1 to C12 straight or branched chain hydrocarbon that is unsubstituted, or substituted with 1 to 3 F, Cl, $CF_3$, $CF_2CF_3$, $CHF_2$, $CH_2F$, $OCF_3$, CN, or a combination thereof, preferably a C1 to C8 straight or branched chain hydrocarbon that is unsubstituted, or substituted with 1 to 3 of F, Cl, $CF_3$, $CF_2CF_3$, $CHF_2$, $CH_2F$, $OCF_3$, CN, NCS, or a combination thereof, more preferably a C1 to C4 straight or branched chain hydrocarbon that is unsubstituted, or substituted with 1 to 3 of F, or 1 of Cl, $CF_3$, $CF_2CF_3$, $CHF_2$, $CH_2F$, $OCF_3$, CN, NCS.

An "alkyloxy" group as used herein means an alkyl group as defined above attached to a carbon atom via an ether oxygen.

An "alkenyl" group as used herein means a C2 to C12 straight or branched chain hydrocarbon having one or more unsaturations, and that is unsubstituted, or substituted with 1 to 3 of F, Cl, $CF_3$, $CF_2CF_3$, $CHF_2$, $CH_2F$, $OCF_3$, CN, NCS, or a combination thereof, preferably a C2 to C8 straight or branched chain hydrocarbon that is unsubstituted, or substituted with 1 to 3 of F, Cl, $CF_3$, $CF_2CF_3$, $CHF_2$, $CH_2F$, $OCF_3$, CN, or a combination thereof, more preferably a C2 to C4 straight or branched chain hydrocarbon that is unsubstituted, or substituted with 1 to 3 of F, Cl, $CF_3$, $CF_2CF_3$, $CHF_2$, $CH_2F$, $OCF_3$, or CN.

The number of carbon atoms of a group is independent of the number of substituents. For example a $CH_2CH_3CF_2CF_3$ group is a C2 alkyl substituted with $CF_2CF_3$.

Hereinafter, a compound, a liquid crystal composition including the compound, and a liquid crystal display including the liquid crystal composition will be described in detail with reference to the accompanying drawings.

In an exemplary embodiment, a compound is represented by Chemical Formula 1.

[Chemical Formula 1]

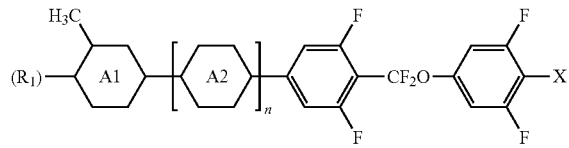

In Chemical Formula 1, n is 0, 1, or 2, and ($R_1$) is hydrogen or a C1 to C15 alkyl. In this case, at least one $CH_2$ group of the C1 to C15 alkyl may be independently replaced with —C≡C—, —$CF_2O$—, —CH=CH—, —O—, —CO—O—, —O—CO—, or —O—CO—O— in a way that oxygen atoms, if present, are directly connected to each other, and 1 to 3 hydrogen atoms may be replaced with a halogen.

The element represented by "X" is F, Cl, $CF_3$, $CF_2CF_3$, $CHF_2$, $CH_2F$, $OCF_3$, CN, NCS, or a C1 to C5 alkyl including 1 to 3 elements represented by F. In this regard, when X is a C1 to C5 alkyl including 1 to 3 fluoro substituents and a $CH_2$ group may be independently substituted with one or more oxygen atoms.

(F) indicates that fluoro may be substituted or unsubstituted.

Each of

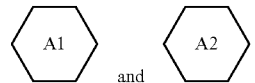

may independently be

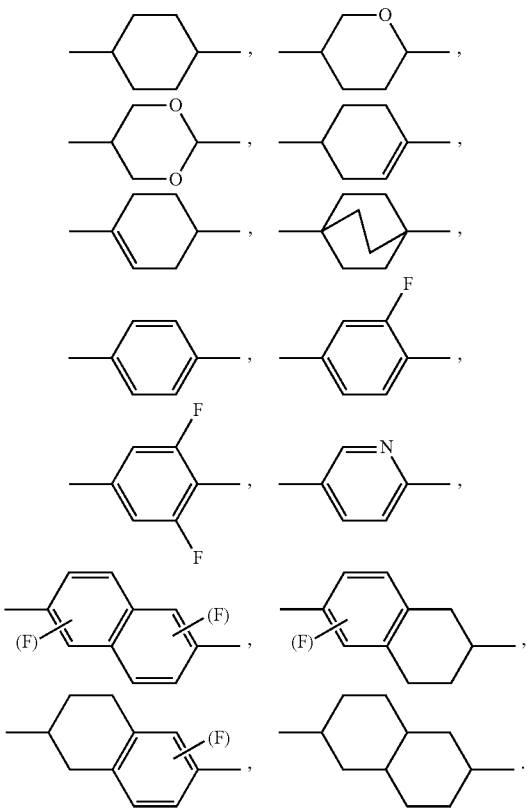

The compound represented by Chemical Formula 1 may include one or more compounds represented by Chemical Formula 1-1 to Chemical Formula 1-14.

(1-1)

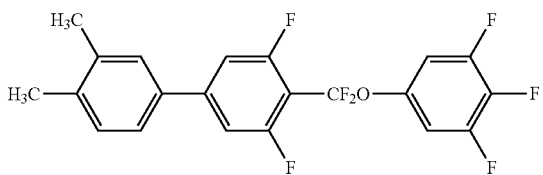

(1-2)

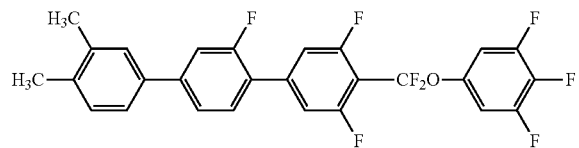

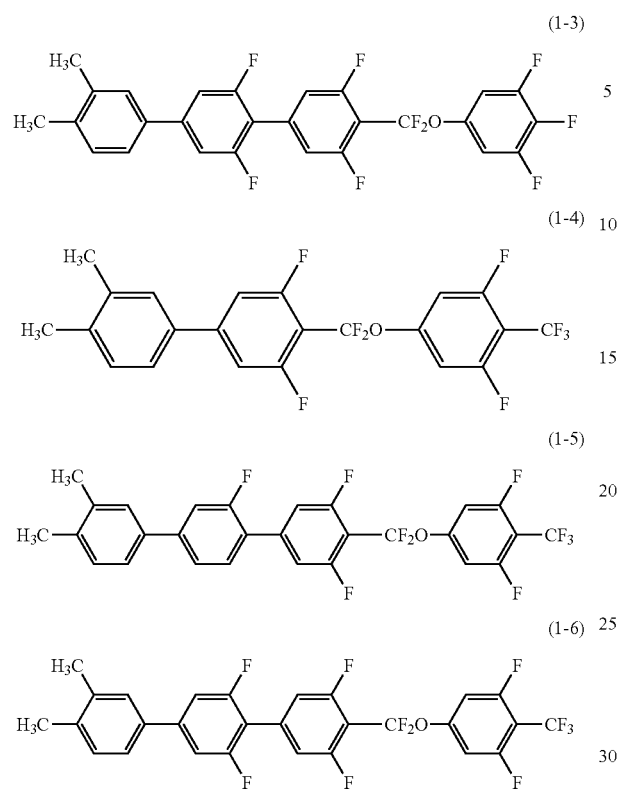
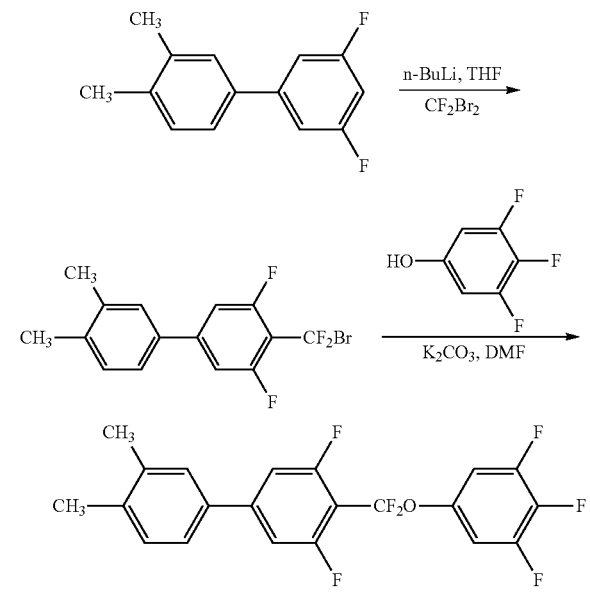
Further, a process of manufacturing the compound represented by Chemical Formula 1-2 may be schematized as follows.
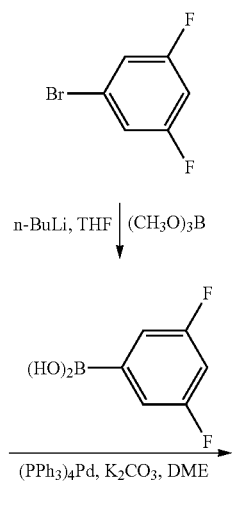
A process of manufacturing the compound represented by Chemical Formula 1-1 may be schematized as follows.
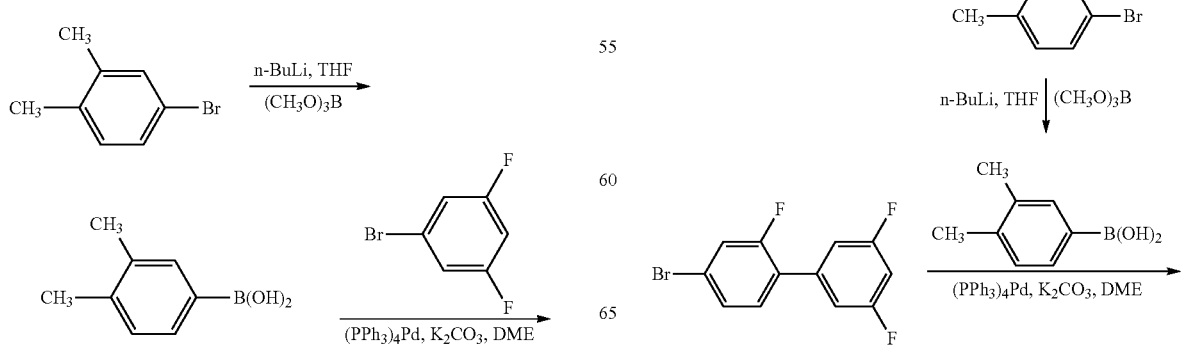

21
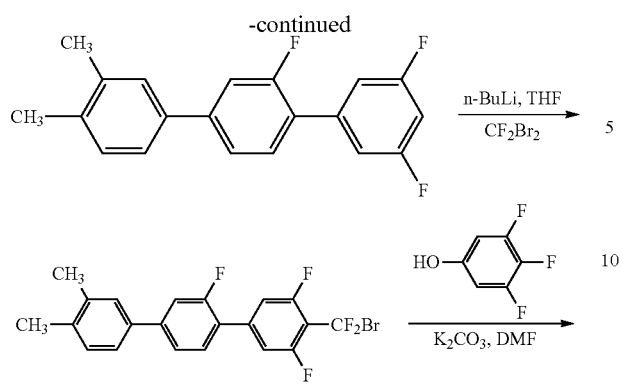
22
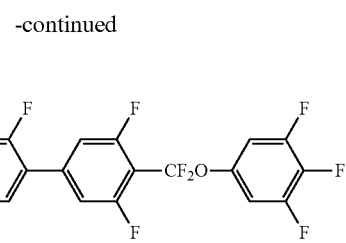
A process of manufacturing the compound represented by Chemical Formula 1-8 may be schematized as follows.
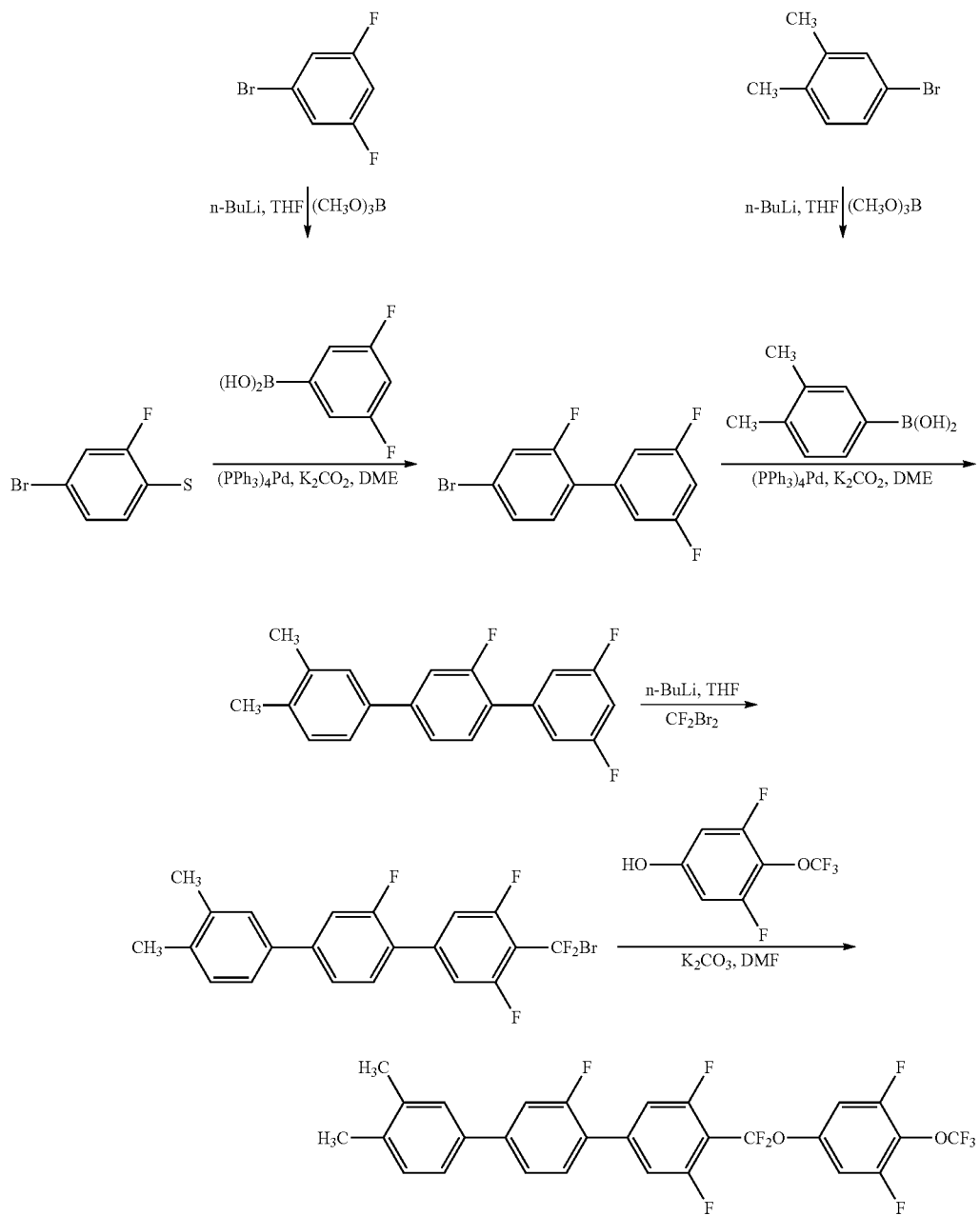

Although the manufacturing processes for some of the compounds represented by Chemical Formula 1 have been schematized, the manufacturing processes are not limited thereto.

These new compounds may have advantageous rotational viscosity characteristics when applied to a liquid crystal composition as compared with a compound having a conventional structure. Without being limited by theory, it is believed that the improved rotational viscosity may be attributed to the inclusion of a methyl substituent in a meta direction (i.e. meta position) of a phenyl group. This will be described later in detail.

Hereinafter, an exemplary embodiment of a liquid crystal composition will be described. The liquid crystal composition includes one or more compound represented by Chemical Formula 1.

[Chemical Formula 1]

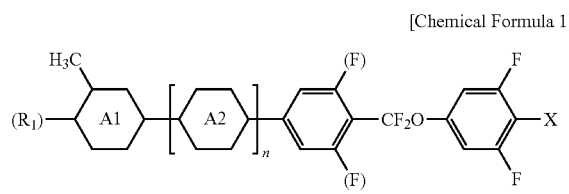

In Chemical Formula 1, n is 0, 1, or 2, and ($R_1$) is hydrogen or a C1 to C15 alkyl. When $R_1$ is a C1 to C15 alkyl, at least one $CH_2$ group may be independently replaced with —C≡C—, —$CF_2$O—, —CH=CH—, —O—, —CO—O—, —O—CO—, or —O—CO—O— in a manner such that oxygen atoms are directly connected to each other, and 1 to 3 hydrogen atoms may be replaced with a halogen.

The element represented by X is F, Cl, $CF_3$, $CF_2CF_3$, $CHF_2$, $CH_2F$, $OCF_3$, CN, NCS, or a C1 to C5 alkyl including 1 to 3 elements represented by F. In this regard, a $CH_2$ group of the C1 to C5 alkyl may be independently substituted with one or more oxygen atoms.

(F) indicate that a fluoro may be substituted or unsubstituted.

Each of

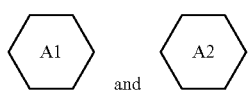

may independently be

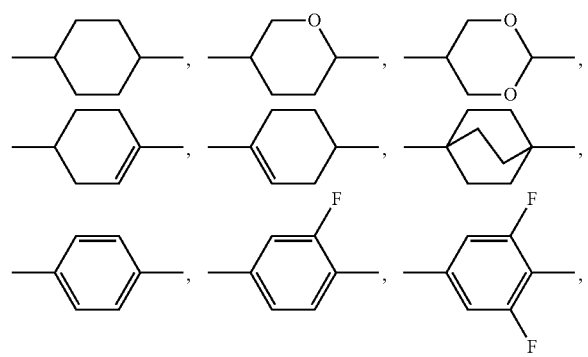

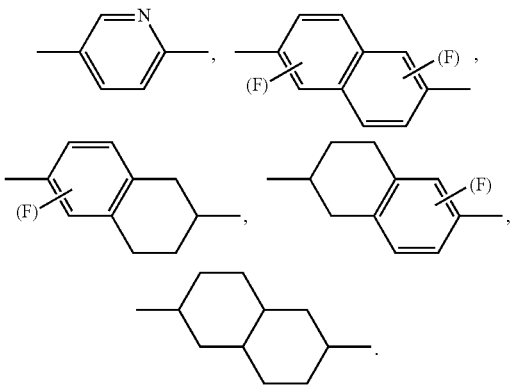

The compound represented by Chemical Formula 1 may include one of more compounds represented by Chemical Formula 1-1 to Chemical Formula 1-14.

(1-1)

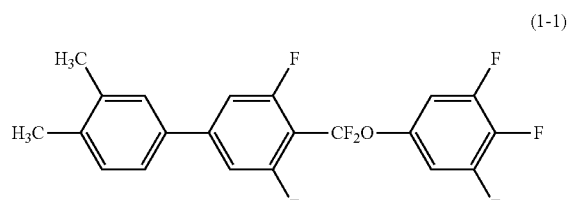

(1-2)

(1-3)

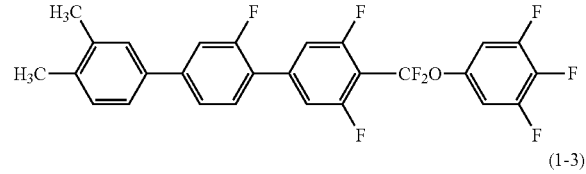

(1-4)

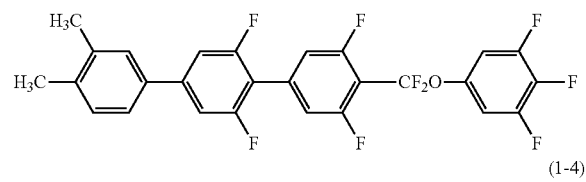

(1-5)

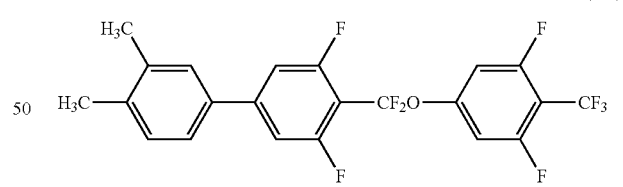

(1-6)

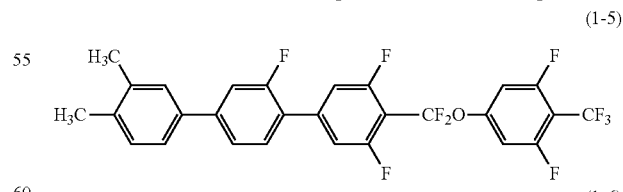

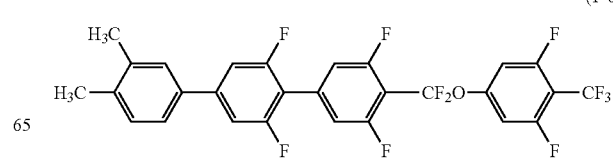

-continued (1-7)

[Structure: H3C, H3C substituted phenyl - F,F phenyl - CF2O - F,F phenyl - CF3]

(1-8)

[Structure: H3C, H3C substituted phenyl - F phenyl - F,F phenyl - CF2O - F,F phenyl - CF3]

(1-9)

[Structure: H3C, H3C substituted phenyl - F,F phenyl - F,F phenyl - CF2O - F,F phenyl - CF3]

(1-10)

[Structure: H3C, H3C substituted phenyl - phenyl - F,F phenyl - CF2O - F,F phenyl - F]

(1-11)

[Structure: H3C, H3C substituted phenyl - tetrahydropyran - F,F phenyl - CF2O - F,F phenyl - F]

(1-12)

[Structure: H3C, H3C substituted phenyl - phenyl - F,F phenyl - CF2O - F,F phenyl - CF3]

(1-13)

[Structure: H3C, H3C substituted phenyl - dioxane - F,F phenyl - CF2O - F,F phenyl - F]

(1-14)

[Structure: H3C, H3C substituted phenyl - tetrahydropyran - F,F phenyl - CF2O - F,F phenyl - CF3]

In a total liquid crystal composition, the content of the compound represented by Chemical Formula 1 may be in a range of about 1 wt % to about 30 wt %. More specifically, the compound of Chemical Formula 1 may be in a range of about 5 wt % to about 20 wt %, or even more specifically, may be in a range of about 5 wt % to about 15 wt % of the total weight of the liquid crystal composition.

If the content of the compound represented by Chemical Formula 1 is less than about 1 wt % of the total liquid crystal composition, it is difficult to achieve a low viscosity effect.

Further, if the content of the compound represented by Chemical Formula 1 exceeds about 30 wt % of the total liquid crystal composition, low temperature stability may be reduced.

The liquid crystal composition may include one or more of the compounds represented by Chemical Formula 2.

[Chemical Formula 2]

$$R_1-\text{[cyclohexyl]}-\text{[cyclohexyl]}-R_2$$

In Chemical Formula 2, $R_1$ and $R_2$ independently indicate C1 to C12 alkyl, C1 to C12 alkoxy, or C2 to C12 alkenyl.

A content of the compound represented by Chemical Formula 2 may be in a range of about 5 wt % to about 60 wt % of the total liquid crystal composition.

The liquid crystal composition may include one or more of the compound represented by Chemical Formula 3.

[Chemical Formula 3]

$$R_3-\text{A1}-\text{A2}-\text{A3}-R_4$$

Each of $$\text{A1}, \text{A2}, \text{A3}$$

may independently be

[Various ring structures: cyclohexyl, tetrahydropyran (two orientations), dioxane, cyclohexenyl (two orientations), bicyclic, phenyl, fluorophenyl, difluorophenyl, pyridyl, fluorinated naphthalenyl structures, fluorinated decalin structures, decalin].

(F) indicates that a fluoro is optionally substituted in place of a hydrogen, $R_3$ and $R_4$ independently indicate C1 to C12 alkyl, C1 to C12 alkoxy, or C2 to C12 alkenyl.

A content of the compound represented by Chemical Formula 3 may be in a range of about 1 wt % to about 40 wt % of the total liquid crystal composition.

The liquid crystal composition may include one or more of the compound represented by Chemical Formula 4.

[Chemical Formula 4]

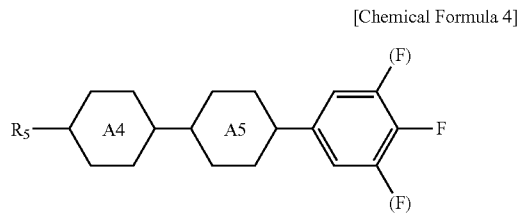

Each of

may independently be

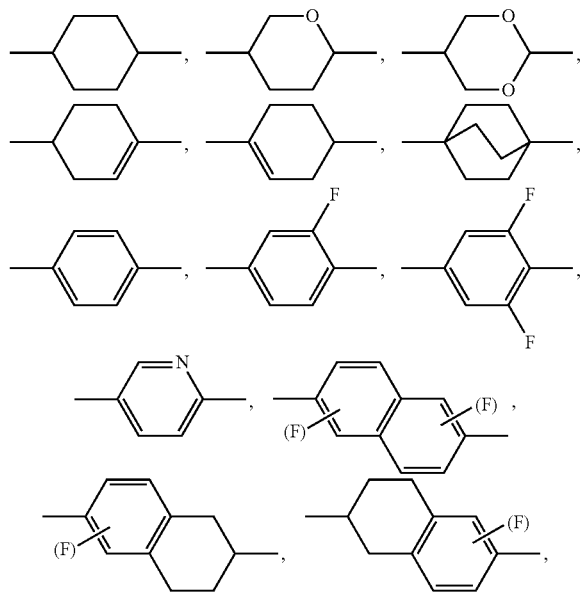

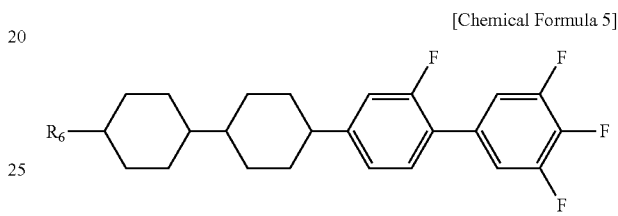

$R_5$ indicates C1 to C12 alkyl, C1 to C12 alkoxy, or C2 to C12 alkenyl, and (F) indicates that a fluoro may be substituted or unsubstituted.

A content of the compound represented by Chemical Formula 4 may be in a range of about 1 wt % to about 40 wt % of the total liquid crystal composition.

The liquid crystal composition may include one or more of the compound represented by Chemical Formula 5.

[Chemical Formula 5]

$R_6$ indicates C1 to C12 alkyl, C1 to C12 alkoxy, or C2 to C12 alkenyl.

A content of the compound represented by Chemical Formula 5 may be in a range of about 1 wt % to about 15 wt % of the total liquid crystal composition.

In an exemplary embodiment, the liquid crystal composition includes the compound represented by Chemical Formula 1, and may further include all of the compounds represented by Chemical Formulae 2 to 5, or may further include only some of the compounds represented by Chemical Formulae 2 to 5.

In other words, the exemplary liquid crystal composition necessarily includes the compound represented by Chemical Formula 1, and may further optionally include the compounds represented by Chemical Formulae 2 to 5 in an appropriate ratio as needed.

Hereinafter, of the properties of the exemplary liquid crystal compound will be described.

The phase transition temperature (Tni), refractive index Δn, dielectric anisotropy (Δε), and rotational viscosity (γ1) were measured for two exemplary new compounds (Examples 1 and 2) and three comparative example compounds (Comparative Examples 1-3).

TABLE 1

| | | Structure | Tni | Δn | Δε | γ1 |
|---|---|---|---|---|---|---|
| 3 ring | Comparative Example 1 | 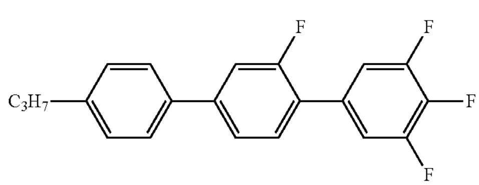 | 48 | 0.21 | 20 | 156 |

TABLE 1-continued

| | Structure | Tni | Δn | Δε | γ1 |
|---|---|---|---|---|---|
| Comparative Example 2 | C₃H₇–[phenyl]–[phenyl-F,F]–CF₂O–[phenyl-F,F]–F | 0 | 0.13 | 23 | 102 |
| Example 1 (Chemical Formula 1-1) | H₃C, H₃C–[phenyl]–[phenyl-F,F]–CF₂O–[phenyl-F,F]–F | −51 | 0.08 | 19 | 96 |
| 4 ring Comparative Example 3 | H₃C–[phenyl]–[phenyl-F]–[phenyl-F,F]–CF₂O–[phenyl-F,F]–F | 99 | 0.20 | 31 | 232 |
| Example 2 (Chemical Formula 1-8) | H₃C, H₃C–[phenyl]–[phenyl-F]–[phenyl-F,F]–CF₂O–[phenyl-F,F]–OCF₃ | 66 | 0.17 | 20 | 148 |

As shown in Table 1, the rotational viscosity is reduced in the compounds of Examples 1 and 2 as compared with the compounds of Comparative Examples 1 to 3.

Referring to Table 1, the structure of the compounds according to Examples 1 and 2 includes a methyl substituent attached to a phenyl group in the meta direction (i.e. meta position). However, the methyl substituent is not included in the compounds of the comparative examples.

For example, when the compound includes 3-ring structures, the rotation viscosity is reduced in the compound including the methyl substituent in the meta direction as represented by Chemical Formula 1-1 (Example 1) when compared with the compounds according to Comparative Examples 1 and 2.

Similarly, in the case of a compound including 4-ring structures, the rotation viscosity is significantly ameliorated in the compound including the methyl substituent as represented by Chemical Formula 1-8 (Example 2) when compared with the compound according to Comparative Example 3.

Hereinafter, a result of measuring the property of an exemplary embodiment of a liquid crystal composition will be described.

Table 2 shows properties of the liquid crystal compositions according to Comparative Example 1 and Examples 4 to 6. Further, Table 3 shows the structure and amount of each compound included in the liquid crystal compositions according to Comparative Example 2 and Examples 4-6.

TABLE 2

| Property | Comparative Example 2 (C2) | Example 4 (E4) | Example 5 (E5) | Example 6 (E6) |
|---|---|---|---|---|
| Dielectric anisotropy (Δε), | 4.5 | 4.6 | 4.4 | 4.3 |
| Tni | 79 | 78 | 79 | 74 |
| Δn | 0.110 | 0.110 | 0.110 | 0.110 |
| rotation viscosity (γ1) | 53 | 46 | 44 | 45 |

TABLE 3

| | Single group (Content, wt %) | R1 | R2 | C2 (wt %) | E4 (wt %) | E5 (wt %) | E6 (wt %) |
|---|---|---|---|---|---|---|---|
| 1 | C₃H₇–[cyclohexyl]–[cyclohexyl]–CH=CH₂ | — | — | 36.2 | 38.1 | 38.0 | 39.0 |
| 2 | C₃H₇–[cyclohexyl]–[cyclohexyl]–[cyclohexyl]–CH=CH₂ | — | — | 9.4 | 10.8 | 9.0 | 8.0 |

TABLE 3-continued
| | Single group (Content, wt %) | R1 | R2 | C2 (wt %) | E4 (wt %) | E5 (wt %) | E6 (wt %) |
|---|---|---|---|---|---|---|---|
| 3 |  | C3H7<br>C5H11 | C2H5<br>C2H5 | 4.5<br>4.2 | 4.3<br>3.9 | 4.0<br>4.0 | 3.0<br>— |
| 4 |  | — | — | 5.2 | 4.9 | 6.2 | 4.5 |
| 5 | 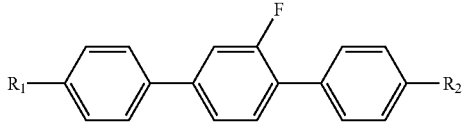 | C2H5<br>C3H7 | C3H7<br>C3H7 | 2.6<br>1.6 | 4.3<br>3.1 | 6.0<br>— | 2.8<br>— |
| 6 | 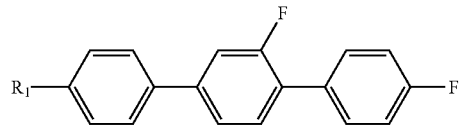 | C2H5<br>C3H7 | —<br>— | —<br>— | —<br>— | 6.8<br>— | 9.7<br>4.9 |
| 7 | 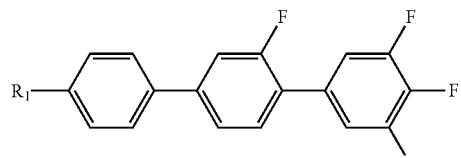 | C2H5<br>C3H7<br>C5H11 | —<br>—<br>— | 2.4<br>7.5<br>8.0 | 6.3<br>3.9<br>— | —<br>—<br>— | —<br>—<br>— |
| 8 | 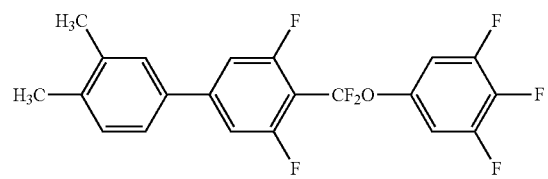 | — | — | — | 7.5 | 9.0 | 5.0 |
| 9 | 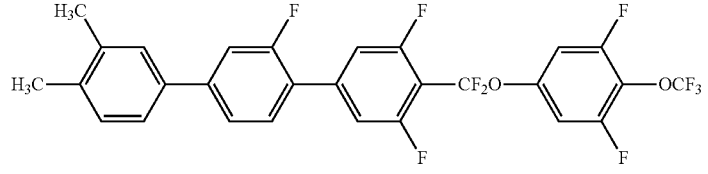 | — | — | — | — | 3.0 | 4.0 |
| 10 | 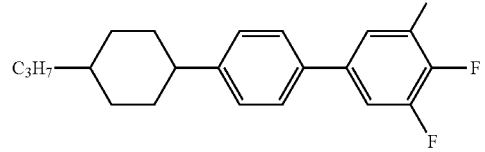 | — | — | 5 | — | 4.0 | 8.3 |
| 11 | 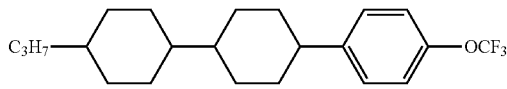 | — | — | 4.5 | 6.2 | 2.0 | 7.5 |
| 12 | 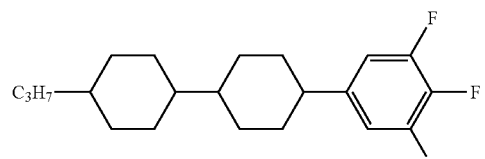 | — | — | 7.0 | — | — | — |

TABLE 3-continued

| Single group (Content, wt %) | R1 | R2 | C2 (wt %) | E4 (wt %) | E5 (wt %) | E6 (wt %) |
|---|---|---|---|---|---|---|
| 13 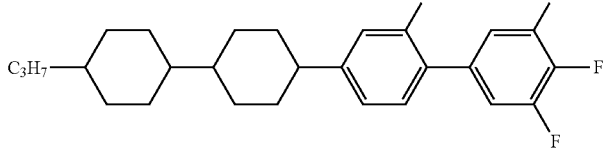 | — | — | 2.1 | 6.7 | 8.0 | 3.3 |

Referring to Table 2, the rotation viscosity (γ1) is ameliorated in the liquid crystal composition including the compound represented by Chemical Formula 1 (according to Examples 4 to 6) while it still has the same levels of Tni, Δn, and dielectric anisotropy (Δ∈) as the liquid crystal composition of Comparative Example 2.

Table 3 shows the structure and the amount of individual liquid crystal compounds included in the liquid crystal compositions for each of the comparative examples and examples. Referring to Table 3, the liquid crystal composition according to the Examples may have a reduced total amount of the terphenyl-based (#7) liquid crystal single groups (Example 4) or no terphenyl-based (#7) liquid crystal single group (Examples 5 and 6).

However, referring to Table 2, as shown in the Examples, it is possible to ameliorate the rotation viscosity characteristic of the liquid crystal composition while having the same or similar level of dielectric anisotropicity by reducing the content of the terphenyl-based liquid crystal single group or by not including the terphenyl-based liquid crystal single group in the liquid crystal composition.

In brief, since having high dielectric anisotropy, the terphenyl-based compound generally needs to be included in the liquid crystal composition at a predetermined ratio. However, in the present exemplary embodiment, when the liquid crystal composition includes the compound represented by Chemical Formula 1, it is possible to maintain the same or improved characteristics while simultaneously reducing the content of the terphenyl-based liquid crystal single group.

Specifically, it is possible to accomplish the same or similar performance by using a single compound substituted with a methyl group at a meta position (i.e. the compound represented by Chemical Formula 1) without the need to include a terphenyl-based compound which is typically used as an essential component of a conventional liquid crystal composition.

Hereinafter, a liquid crystal display including the above-described liquid crystal composition will be described with reference to FIG. 1 and FIG. 2. However, the structure of the liquid crystal display to be described below is merely an example, and the liquid crystal composition may be applied to alternative structures of the liquid crystal display.

Figure 2:
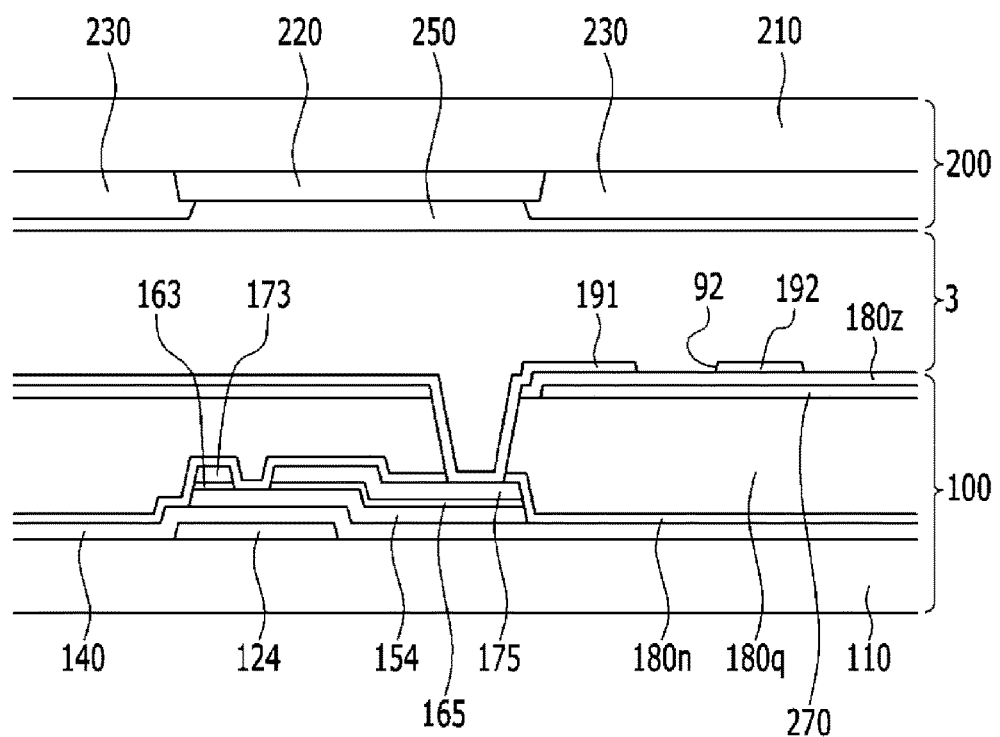
FIG. 2 illustrates a cross-sectional view of a contact hole of a gate driver of an exemplary embodiment of a display device, which is taken along a line II-II of the plan view of FIG. 1.

FIG. 1 is a plan view illustrating a portion of a pixel area of an exemplary embodiment of a display device, and FIG. 2 illustrates a cross-sectional view of a contact hole of a gate driver which is taken along a line II-II of the exemplary display device of FIG. 1.

A gate conductor including a gate line 121 is formed on an insulation substrate 110. The insulation substrate 110 may be made of transparent glass, plastic, or the like.

The gate line 121 includes a gate electrode 124 and a wide end portion (not illustrated) for connection with another layer or an external driving circuit. The gate line 121 may be made of an aluminum-based metal such as aluminum (Al) or an aluminum alloy, a silver-based metal such as silver (Ag) or a silver alloy, a copper-based metal such as copper (Cu) or a copper alloy, a molybdenum-based metal such as molybdenum (Mo) or a molybdenum alloy, chromium (Cr), tantalum (Ta), or titanium (Ti). The gate line 121 may have a multilayered structure including at least two conductive layers having different physical properties.

A gate insulating layer 140 made of a silicon nitride (SiNx), a silicon oxide (SiOx), or the like, is formed on the gate line 121. The gate insulating layer 140 may have a multilayered structure including at least two insulating layers having different physical properties.

A semiconductor 154 made of amorphous silicon or polysilicon is formed on the gate insulating layer 140. The semiconductor 154 may further include an oxide semiconductor.

Ohmic contacts 163 and 165 may be positioned on the semiconductor 154. The ohmic contacts 163 and 165 may be made of a material such as n+ hydrogenated amorphous silicon in which an n-type impurity such as phosphorus is doped at a high concentration, or of a silicide. The ohmic contacts 163 and 165 may form a pair to be disposed on the semiconductor 154. In the case where the semiconductor 154 is an oxide semiconductor, the ohmic contacts 163 and 165 may be omitted.

A data conductor including a data line 171, a source electrode 173 and a drain electrode 175, is formed on the ohmic contacts 163 and 165 and the gate insulating layer 140.

The data line 171 includes a wide end portion (not illustrated) for connection with another layer or an external driving circuit. The data line 171 transfers a data signal and mainly extends in a vertical direction to cross the gate line 121.

In this case, the data line 171 may have a first curved portion having a curved shape in order to acquire maximum transmittance of the liquid crystal display, and the curved portion meets another in a middle region of the pixel area to have a V-lettered shape. A second curved portion which is curved to form a predetermined angle with the first curved portion may be further included in the middle region of the pixel area.

The first curved portion of the data line 171 may be bent at an angle of about 7° with respect to a vertical reference line which forms an angle of 90° with respect to a direction in which the gate line 121 is extended. The second curved portion disposed at the center area of the pixel area may be further bent to form an angle of about 7° to about 15° with respect to the first curved portion.

The source electrode 173 is a part of the data line 171, and is disposed on the same line as the data line 171. The drain electrode 175 is formed to extend in parallel with the source electrode 173. Accordingly, the drain electrode 175 is parallel with a portion of the data line 171.

The gate electrode 124, the source electrode 173, and the drain electrode 175 constitute one thin film transistor (TFT) together with the semiconductor 154, and a channel of the thin film transistor is positioned in the semiconductor 154 between the source electrode 173 and the drain electrode 175.

In an exemplary embodiment, the liquid crystal display includes the source electrode 173 disposed on the same line as the data line 171, and the drain electrode 175 extended in parallel with the data line 171, thereby broadening the width of the thin film transistor without widening the area occupied by the data conductor and thus increasing the aperture ratio of the liquid crystal display.

The data line 171 and the drain electrode 175 may be made of a refractory metal such as molybdenum, chromium, tantalum, and titanium, or an alloy thereof. The data line 171 and the drain electrode 175 may have a multilayer structure including a refractory metal layer (not shown) and a low resistance conductive layer (not shown). An example of the multilayered structure may include a double layer including a chromium, molybdenum, or molybdenum alloy lower layer and an aluminum or aluminum alloy upper layer, and a triple layer including a molybdenum or molybdenum alloy lower layer, an aluminum or aluminum alloy intermediate layer, and a molybdenum or molybdenum alloy upper layer. However, the data line 171 and the drain electrode 175 may be made of other various metals or conductors in addition to the described metals. A width of the data line 171 may be about 3.5 micrometers (μm)±0.75 μm.

A first passivation layer 180n is disposed on the data line 171, source electrode 173, drain electrode 175, the gate insulating layer 140, and the exposed semiconductor 154. The first passivation layer 180n may be formed of an organic insulating material or an inorganic insulating material.

A second passivation layer 180q is disposed on the first passivation layer 180n. The second passivation layer 180q is optional and may be omitted. The second passivation layer 180q may be a color filter. The second passivation layer 180q may uniquely display one of the primary colors if it is the color filter, and the primary colors may be, for example, three primary colors such as red, green, and blue, or yellow, cyan, magenta, and the like. Although not illustrated, a color filter 230 for displaying mixed colors of the primary colors or white, as well as the primary colors, may be further included.

A second electrode 270 is formed on the second passivation layer 180q. The second electrode 270 may have a planar shape, and may be formed as a plate on the entire substrate 110. The second electrode 270 may have an opening (not illustrated) disposed in a region corresponding to a periphery of the drain electrode 175. That is, the second electrode 270 may have a plate-like plane shape.

The second electrodes 270 positioned at adjacent pixels are connected to each other to receive a common voltage having a predetermined magnitude supplied from outside of the display area.

A third passivation layer 180z is disposed on the second electrode 270. The third passivation layer 180z may be made of an organic insulating material, an inorganic insulating material, or the like.

A first electrode 191 is formed on the third passivation layer 180z. The first electrode 191 includes a curved edge that is almost parallel to the first curved portion and the second curved portion of the data line 171. The first electrode 191 has a plurality of first cutouts 92, and includes a plurality of first slit electrodes 192 defined by the plurality of first cutouts 92.

A first contact hole 185 exposing the drain electrode 175 is formed in the first passivation layer 180n, the second passivation layer 180q, and the third passivation layer 180z. The first electrode 191 is physically and electrically connected to the drain electrode 175 through the first contact hole 185 to receive a voltage from the drain electrode 175.

Although not illustrated, an alignment layer is coated on the first electrode 191 and the third passivation layer 180z. The alignment layer may be a horizontal alignment layer and may be rubbed in a predetermined direction. However, in accordance with another exemplary embodiment of a liquid crystal display, the alignment layer may include a photoreactive material and may be photoaligned.

The first electrode 191 may be a pixel electrode and the second electrode 270 may be a common electrode.

The second display panel 200 will now be described.

A light blocking member 220 is formed on an insulating substrate 210 made of transparent glass, plastic, or the like. The light blocking member 220 is also called a black matrix and serves to prevent light leakage.

A plurality of color filters 230 are formed on the substrate 210. In the case where the second passivation layer 180q in the lower display panel 100 is a color filter, the color filter 230 of the upper display panel 200 may be omitted. Further, the light blocking member 220 of the upper display panel 200 may also be formed in the lower display panel 100.

An overcoat 250 is formed on the color filter 230 and the light blocking member 220. The overcoat 250 may be made of an insulating material (e.g. an organic insulating material), and prevents the color filter 230 from being exposed and provides a flat surface. The overcoat 250 is optional and may be omitted.

An alignment layer (not shown) may be disposed on the overcoat 250.

The liquid crystal layer 3 is interposed between the lower display panel 100 and the upper display panel 200. In an exemplary embodiment, the liquid crystal layer 3 may include the liquid crystal composition described above. Long axes of liquid crystal molecules of the liquid crystal layer 3 may be horizontally aligned with respect to surfaces of the two display panels 100 and 200 in a state where there is no electric field applied to the liquid crystal display.

The liquid crystal layer includes a liquid crystal composition including one or more kinds of the compound represented by Chemical Formula 1.

[Chemical Formula 1]

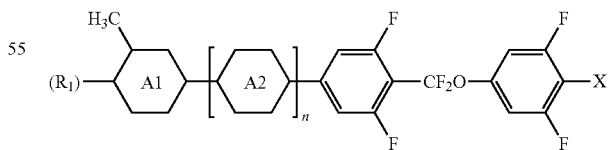

In Chemical Formula 1, n is 0, 1, or 2, and ($R_1$) is hydrogen or a C1 to C15 alkyl. At least one $CH_2$ group of the C1 to C15 alkyl may be independently replaced with —C≡C—, —$CF_2$O—, —CH=CH—, —O—, —CO—O—, —O—CO—, or —O—CO—O— in a way that oxygen atoms are directly connected to each other, and 1 to 3 hydrogen atoms may be replaced with a halogen.

The element represented by X is F, Cl, $CF_3$, $CF_2CF_3$, $CHF_2$, $CH_2F$, $OCF_3$, CN, NCS, or a C1 to C5 alkyl including 1 to 3 elements represented by F. In this regard, when X is the C1 to C5 alkyl, a $CH_2$ group may be independently substituted with one or more oxygen atoms.

(F) indicates that the fluoro group may be substituted or unsubstituted.

Each of $A_1$ and $A_2$ may independently be

[chemical ring structures]

The compound represented by Chemical Formula 1 may include one or more the compounds represented by Chemical Formula 1-1 to Chemical Formula 1-14.

(1-1) through (1-11) [chemical structures]

-continued (1-12)
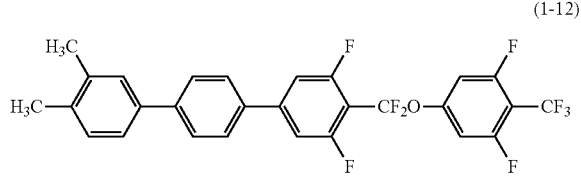

(1-13)
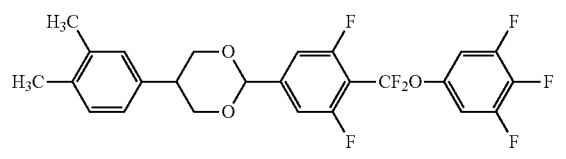

(1-14)
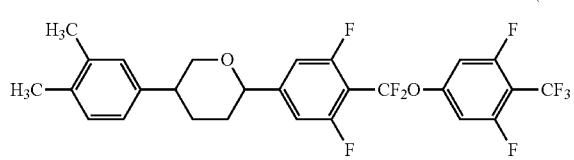

In the total liquid crystal composition, an appropriate content of the compound represented by Chemical Formula 1 may be in a range of about 1 wt % to about 30 wt %. More specifically, the content may be in a range of about 5 wt % to about 20 wt %, or even more specifically, may be in a range of about 5 wt % to about 15 wt %.

When the content of the compound represented by Chemical Formula 1 is less than 1 wt % of the total liquid crystal composition, it is difficult to expect a low viscosity effect.

Further, when the content of the compound represented by Chemical Formula 1 exceeds 30 wt % of the total liquid crystal composition, the low temperature stability may be reduced.

The liquid crystal composition may further include one or more of the compound represented by Chemical Formula 2.

[Chemical Formula 2]

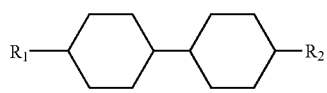

In Chemical Formula 2, $R_1$ and $R_2$ independently indicate C1 to C12 alkyl, C1 to C12 alkoxy, or C2 to C12 alkenyl.

A content of the compound represented by Chemical Formula 2 may be in a range of about 5 wt % to about 60 wt % of the total weight of the liquid crystal composition.

The liquid crystal composition may include one or more of the compound represented by Chemical Formula 3.

[Chemical Formula 3]

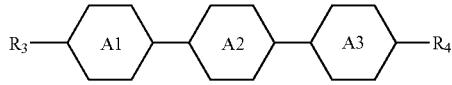

Each of

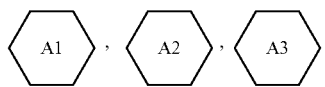

may independently be

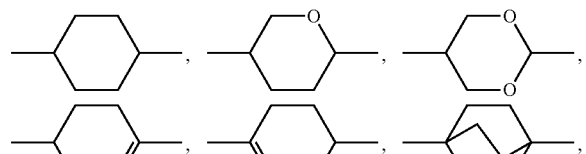

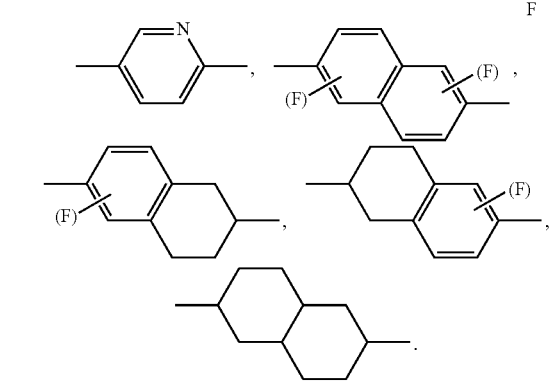

(F) indicates that a fluoro is optionally substituted in place of a hydrogen, $R_3$ and $R_4$ independently indicate C1 to C12 alkyl, C1 to C12 alkoxy, or C2 to C12 alkenyl.

A content of the compound represented by Chemical Formula 3 may be in a range of about 1 wt % to about 40 wt %.

The liquid crystal composition may further include one or more of the compound represented by Chemical Formula 4.

[Chemical Formula 4]

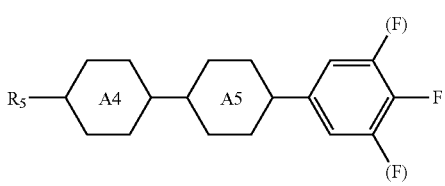

Each of

may independently be

[Chemical structures shown]

R$_5$ indicates C1 to C12 alkyl, C1 to C12 alkoxy, or C2 to C12 alkenyl, and (F) indicates that a fluoro may be substituted or unsubstituted.

A content of the compound represented by Chemical Formula 4 may be in a range of about 1 wt % to about 40 wt % of the total weight of the liquid crystal composition.

The liquid crystal composition may further include one or more of the compound represented by Chemical Formula 5.

[Chemical Formula 5]

[Chemical structure shown]

R$_6$ indicates C1 to C12 alkyl, C1 to C12 alkoxy, or C2 to C12 alkenyl.

A content of the compound represented by Chemical Formula 5 may be in a range of about 1 wt % to about 15 wt % of the total weight of the liquid crystal composition.

In an exemplary embodiment, the liquid crystal composition includes the compound represented by Chemical Formula 1, and may further include all of the compounds represented by Chemical Formulae 2 to 5, or may further include only some of the compounds represented by Chemical Formulae 2 to 5.

In the aforementioned exemplary embodiment, it is described that the first electrode 191 is disposed on the second electrode 270. However, in another exemplary embodiment of a liquid crystal display, the second electrode 270 is disposed on the first electrode 191.

Figure 3:
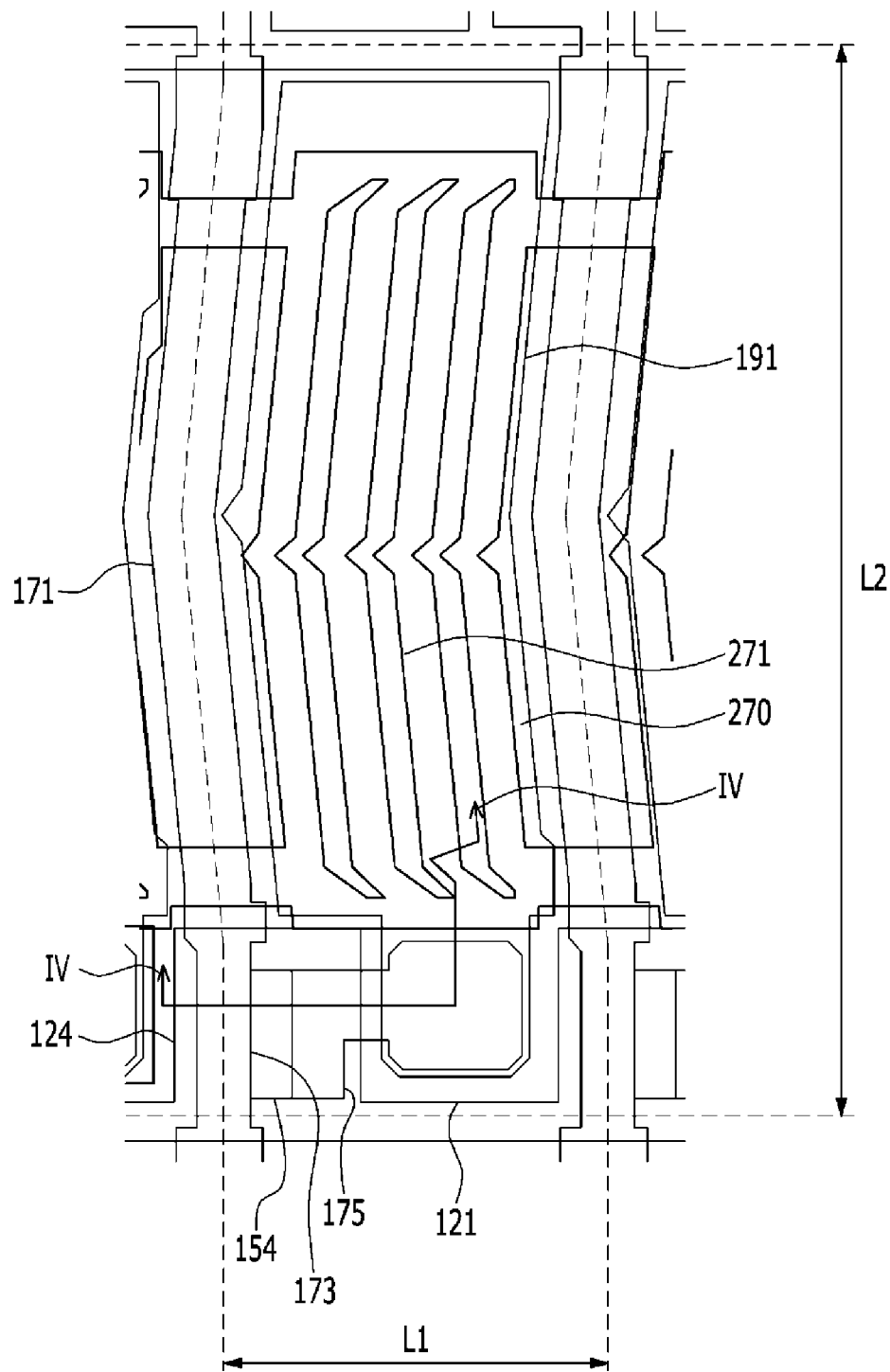
FIG. 3 is a plan view illustrating an exemplary embodiment of a display device.

Hereinafter, an exemplary embodiment of a liquid crystal display will be described with reference to FIG. 3 and FIG. 4. FIG. 3 is a plan view of an exemplary liquid crystal display, and FIG. 4 is a cross-sectional view taken along a line IV-IV of the exemplary embodiment illustrated in FIG. 3.

Figure 4:
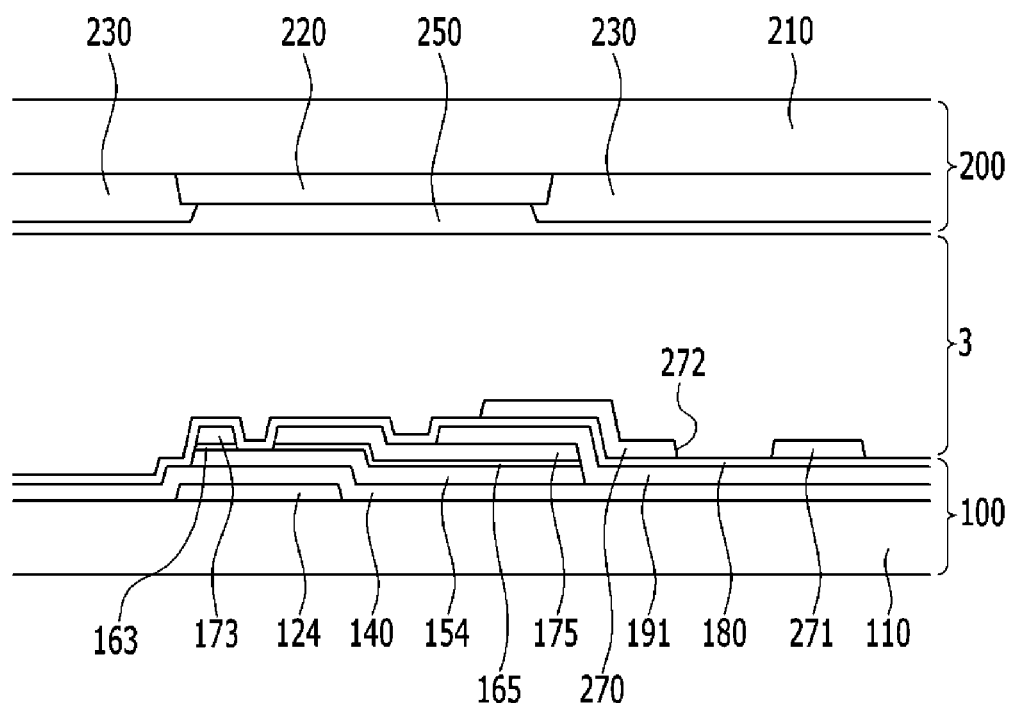
FIG. 4 is a cross-sectional view illustrating the display device taken along a line IV-IV according to the exemplary embodiment illustrated in FIG. 3.

Referring to FIG. 3 and FIG. 4, the exemplary liquid crystal display is substantially similar to the exemplary liquid crystal display illustrated in FIG. 1 and FIG. 2.

First, the lower display panel 100 will be described.

A gate line 121 is formed on an insulation substrate 110.

A gate insulating layer 140 is formed on the gate line 121 that is formed of a silicon nitride (SiNx) or a silicon oxide (SiOx).

A semiconductor 154 is formed on the gate insulating layer 140.

Ohmic contacts 163 and 165 are formed on the semiconductor 154. In the case where the semiconductor 154 is the oxide semiconductor, the ohmic contacts 163 and 165 may be omitted.

A data conductor including a data line 171, a source electrode 173, and a drain electrode 175 is formed on the ohmic contacts 163 and 165 and the gate insulating layer 140.

A first electrode 191 is formed directly on the drain electrode 175. The first electrode 191 has a planar shape, which is a plate shape, and is disposed in one pixel area.

A passivation layer 180 is disposed on the data conductors 171, 173, and 175, the gate insulating layer 140, exposed portions of the semiconductor 154, and the first electrode 191. However, in another exemplary embodiment of a liquid crystal display, a passivation layer 180 may be disposed between the first electrode 191 and the data line 171, and the first electrode 191 may be connected to the drain electrode 175 through a contact hole 185 formed in the passivation layer 180.

The second electrode 270 is formed on the passivation layer 180. Second electrodes 270 are connected to each other to receive common voltages from a common voltage applying unit that is disposed outside of the display area.

The second electrode 270 includes the curved edge which is substantially parallel to the first curved portion and the second curved portion of the data line 171, and the second electrodes 270 disposed at the adjacent pixels are connected to each other. The second electrode 270 includes a plurality of second cutouts 272 and a plurality of second branch electrodes 271 defined by the plurality of second cutouts 272.

Although not illustrated, an alignment layer may be coated on the first electrode 191 and the passivation layer 180. The alignment layer may be a horizontal alignment layer and be rubbed in a predetermined direction However, in another exemplary embodiment of a liquid crystal display, the alignment layer may include a photoreactive material to be photoaligned.

The upper display panel 200 will now be described.

A light blocking member 220 is formed on an insulating substrate 210. A plurality of color filters 230 are formed on the substrate 210. The color filters 230 may be disposed on the lower display panel 100, and in this case, the light blocking member 220 may also be disposed on the lower display panel 100.

An overcoat 250 is formed on the color filter 230 and the light blocking member 220. The overcoat 250 may be omitted.

The alignment layer may be disposed on the overcoat 250.

The liquid crystal layer 3 is interposed between the lower display panel 100 and the upper display panel 200. In an exemplary embodiment, the liquid crystal layer 3 may include the liquid crystal composition which has been previously described. Detailed description of the same constituent elements of the liquid crystal composition is omitted. Specifically, the liquid crystal layer includes one or more of the compound represented by Chemical Formula 1.

[Chemical Formula 1]

$$H_3C-\overset{(R_1)}{\underset{}{A1}}-\left[A2\right]_n-\overset{F}{\underset{F}{\bigcirc}}-CF_2O-\overset{F}{\underset{F}{\bigcirc}}-X$$

In Chemical Formula 1, n is 0, 1, or 2, and $(R_1)$ is hydrogen or a C1 to C15 alkyl. In this case, at least one $CH_2$ group of the C1 to C15 alkyl may be independently replaced with —C≡C—, —$CF_2O$—, —CH=CH—, —O—, —CO—O—, —O—CO—, or —O—CO—O— in a way that oxygen atoms are directly connected to each other, and 1 to 3 hydrogen atoms may be replaced with a halogen.

A substituent represented by "X" is F, Cl, $CF_3$, $CF_2CF_3$, $CHF_2$, $CH_2F$, $OCF_3$, CN, NCS, or a C1 to C5 alkyl including 1 to 3 elements represented by F. In this regard, a $CH_2$ group of the C1 to C5 alkyl may be independently substituted with an oxygen atom.

(F) indicate that a fluoro may be substituted or unsubstituted.

Each of

A1 and A2 may independently be

[ring structures shown]

While this invention has been described in connection with what is presently considered to be practical exemplary embodiments, it is to be understood that the invention is not limited to the disclosed embodiments but, on the contrary, is intended to cover various modifications and equivalent arrangements included within the spirit and scope of the appended claims.

What is claimed is:

1. A compound represented by Chemical Formula 1:

[Chemical Formula 1]

$$H_3C-\overset{(R_1)}{\underset{}{A1}}-\left[A2\right]_n-\overset{F}{\underset{F}{\bigcirc}}-CF_2O-\overset{F}{\underset{F}{\bigcirc}}-X,$$

wherein, in Chemical Formula 1, n is 0, 1, or 2, and a substituent represented by "X" is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms;

$(R_1)$ is hydrogen or a C1 to C15 alkyl, at least one $CH_2$ group being independently replaced with —C≡C—, —$CF_2O$—, —CH=CH—, —O—, —CO—O—, —O—CO—, or —O—CO—O— in a way that oxygen atoms are directly connected to each other, and 1 to 3 hydrogen atoms of the C1 to C15 alkyl being replaced with a halogen;

(F) indicates that a fluoro is optionally substituted in place of a hydrogen; and each of A1 and A2 are independently

2. The compound of claim 1, wherein the compound represented by Chemical Formula 1 comprises one or more compound represented by Chemical Formula 1-1 to Chemical Formula 1-14:

3. A liquid crystal composition comprising a compound represented by Chemical Formula 1:

[Chemical Formula 1]

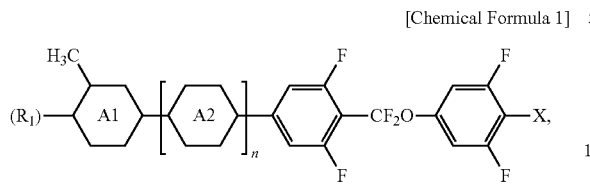

wherein, in Chemical Formula 1, n is 0, 1, or 2, and a substituent represented by X is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms;

($R_1$) is hydrogen or a C1 to C15 alkyl, at least one $CH_2$ group being independently replaced with —C≡C—, —$CF_2$O—, —CH=CH—, —O—, —CO—O—, —O—CO—, or —O—CO—O— in a way that oxygen atoms are directly connected to each other, and 1 to 3 hydrogen atoms of the C1 to C15 alkyl being replaced with halogen;

(F) indicates that a fluoro is optionally substituted in place of hydrogen; and each of

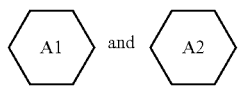

is independently

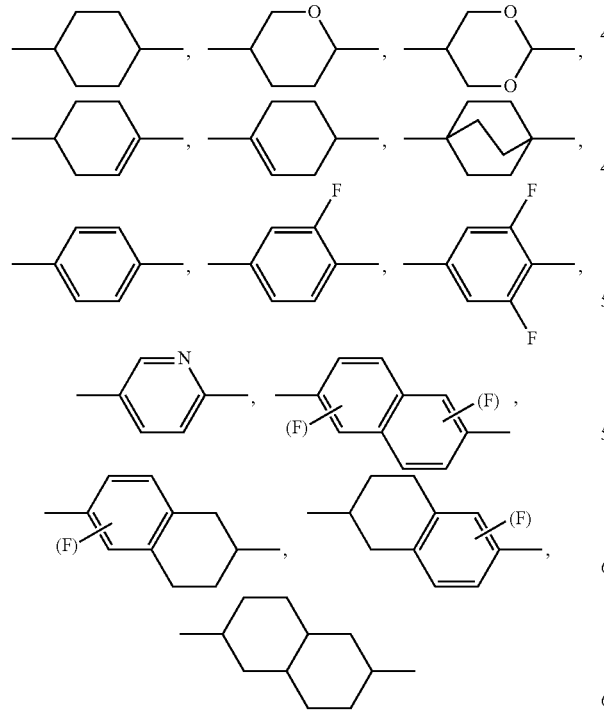

wherein (F) indicates that a fluoro is optionally substituted in place of a hydrogen.

4. The liquid crystal composition of claim 3, wherein the compound represented by Chemical Formula 1 comprises one or more compounds represented by Chemical Formula 1-1 to Chemical Formula 1-14:

(1-1)

(1-2)

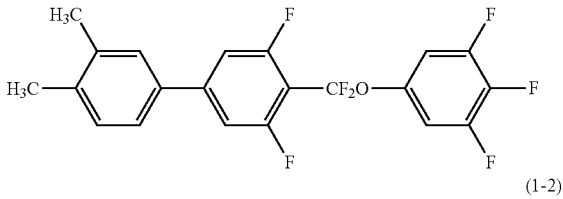

(1-3)

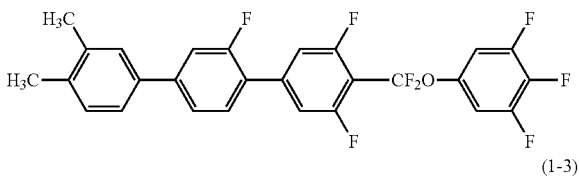

(1-4)

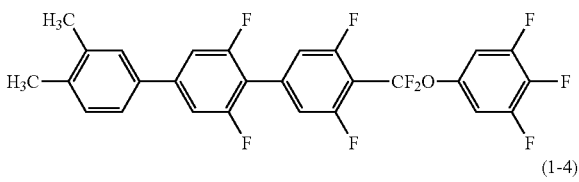

(1-5)

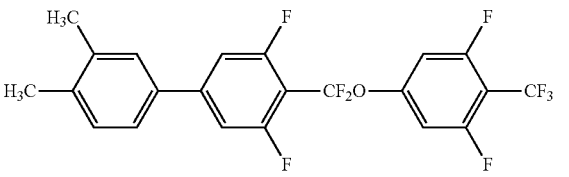

(1-6)

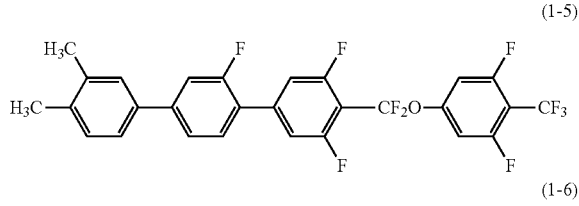

(1-7)

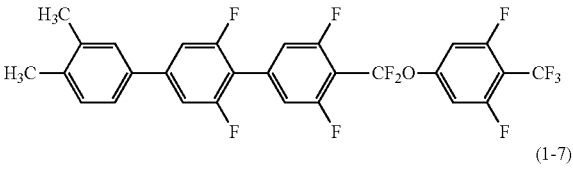

(1-8)

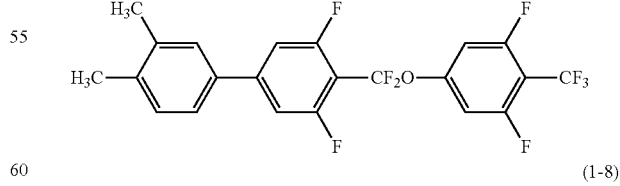

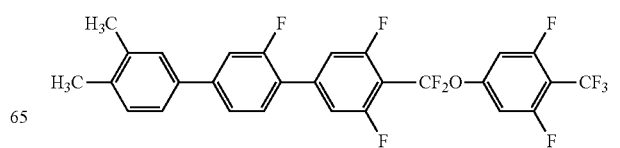

-continued (1-9)

[Structure: H3C, H3C substituted biphenyl-phenyl-CF2O-phenyl with F substituents and CF3]

(1-10)

[Structure with H3C, H3C, F, F, CF2O, F, F]

(1-11)

[Structure with tetrahydropyran ring, H3C, H3C, F, F, CF2O, F, F]

(1-12)

[Structure with H3C, H3C, biphenyl, F, F, CF2O, F, F, CF3]

(1-13)

[Structure with 1,3-dioxane ring, H3C, H3C, F, F, CF2O, F, F]

(1-14)

[Structure with tetrahydropyran, H3C, H3C, F, F, CF2O, F, F, CF3]

5. The liquid crystal composition of claim 3, wherein a content of the compound represented by Chemical Formula 1 is in a range of about 1 wt % to about 30 wt % of the total weight of the liquid crystal composition.

6. The liquid crystal composition of claim 3, wherein the liquid crystal composition further comprises one or more of the compound represented by Chemical Formula 2:

[Chemical Formula 2]

$R_1$—[cyclohexyl-cyclohexyl]—$R_2$, wherein, in Chemical Formula 2, $R_1$ and $R_2$ independently indicate C1 to C12 alkyl, C1 to C12 alkoxy, or C2 to C12 alkenyl.

7. The liquid crystal composition of claim 6, wherein a content of the compound represented by Chemical Formula 2 is in a range of about 5 wt % to about 60 wt % of the total weight of the liquid crystal composition.

8. The liquid crystal composition of claim 3, wherein the liquid crystal composition further comprises one or more of the compound represented by Chemical Formula 3:

[Chemical Formula 3]

$R_3$—A1—A2—A3—$R_4$, wherein each of

A1, A2, A3 is independently

[Various ring structures: cyclohexyl, tetrahydropyran, 1,3-dioxane, cyclohexenyl, cyclohexenyl, bicyclic, phenyl, fluorophenyl, difluorophenyl, pyridyl, naphthyl (F), naphthyl (F), tetrahydronaphthyl (F), tetrahydronaphthyl (F), decalinyl]

wherein (F) indicates that a fluoro is optionally substituted in place of a hydrogen, and $R_3$ and $R_4$ independently indicate C1 to C12 alkyl, C1 to C12 alkoxy, or C2 to C12 alkenyl.

9. The liquid crystal composition of claim 8, wherein a content of the compound represented by Chemical Formula 3 is in a range of about 1 wt % to about 40 wt % of the total weight of the liquid crystal composition.

10. The liquid crystal composition of claim 3, wherein the liquid crystal composition further comprises one or more of the compound represented by Chemical Formula 4:

[Chemical Formula 4]

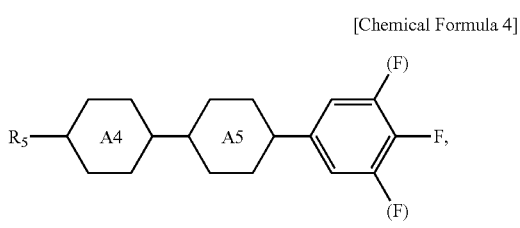

wherein each of

is independently

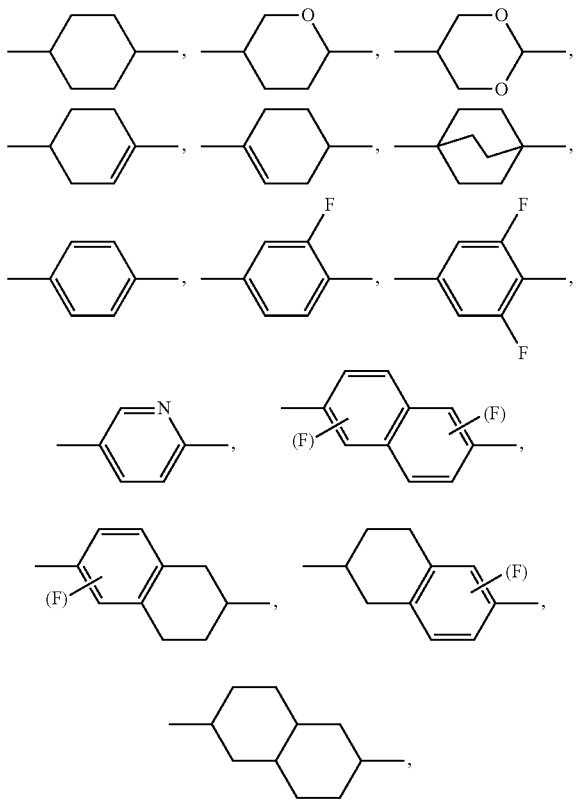

$R_5$ indicates C1 to C12 alkyl, C1 to C12 alkoxy, or C2 to C12 alkenyl, and (F) indicates that a fluoro is optionally substituted in place of a hydrogen.

11. The liquid crystal composition of claim 10, wherein a content of the compound represented by Chemical Formula 4 is in a range of about 1 wt % to about 40 wt % of the total weight of the liquid crystal composition.

12. The liquid crystal composition of claim 3, wherein the liquid crystal composition further comprises one or more of the compound represented by Chemical Formula 5:

[Chemical Formula 5]

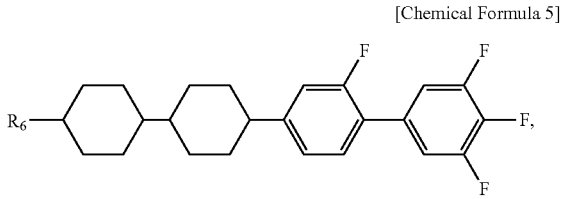

wherein $R_6$ indicates C1 to C12 alkyl, C1 to C12 alkoxy, or C2 to C12 alkenyl.

13. The liquid crystal composition of claim 12, wherein a content of the compound represented by Chemical Formula 5 is in a range of about 1 wt % to about 15 wt % of the total weight of the liquid crystal composition.

14. A liquid crystal display comprising:
a first insulation substrate;
a thin film transistor disposed on the first insulation substrate;
a first electrode connected to the thin film transistor;
a second electrode disposed on the first insulation substrate while being insulated from the first electrode;
a second insulation substrate configured to face the first insulation substrate; and
a liquid crystal layer disposed between the first insulation substrate and the second insulation substrate,
wherein the liquid crystal layer comprises a liquid crystal composition comprising a compound represented by Chemical Formula 1:

[Chemical Formula 1]

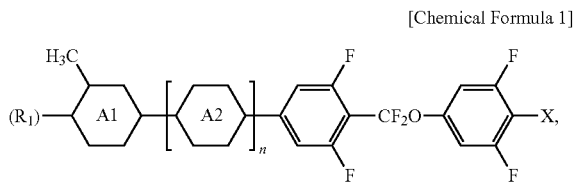

wherein, in Chemical Formula 1, n is 0, 1, or 2, and a substituent represented by X is F, Cl, $CF_3$, $CF_2CF_3$, $CHF_2$, $CH_2F$, $OCF_3$, CN, NCS, or a C1 to C5 alkyl including 1 to 3 fluoro substituents and a $CH_2$ group independently substituted with one or more oxygen atoms;

($R_1$) is hydrogen or a C1 to C15 alkyl, at least one $CH_2$ group being independently replaced with —C≡C—, —$CF_2$O—, —CH—CH—, —O—, —CO—O—, —O—CO—, or —O—CO—O— in a way that oxygen atoms are directly connected to each other, and 1 to 3 hydrogen atoms of the C1 to C15 alkyl being replaced with halogen;

(F) indicates that a fluoro is optionally substituted in place of a hydrogen; and each of

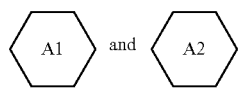

is independently
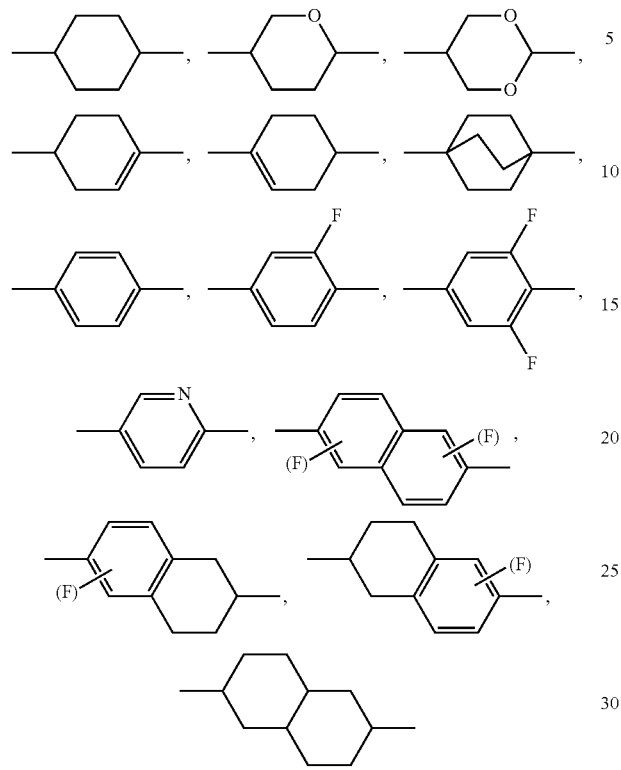
wherein (F) indicates that a fluoro is optionally substituted in place of a hydrogen.
15. The liquid crystal display of claim 14, wherein the compound represented by Chemical Formula 1 comprises one or more compounds represented by Chemical Formula 1-1 to Chemical Formula 1-14:
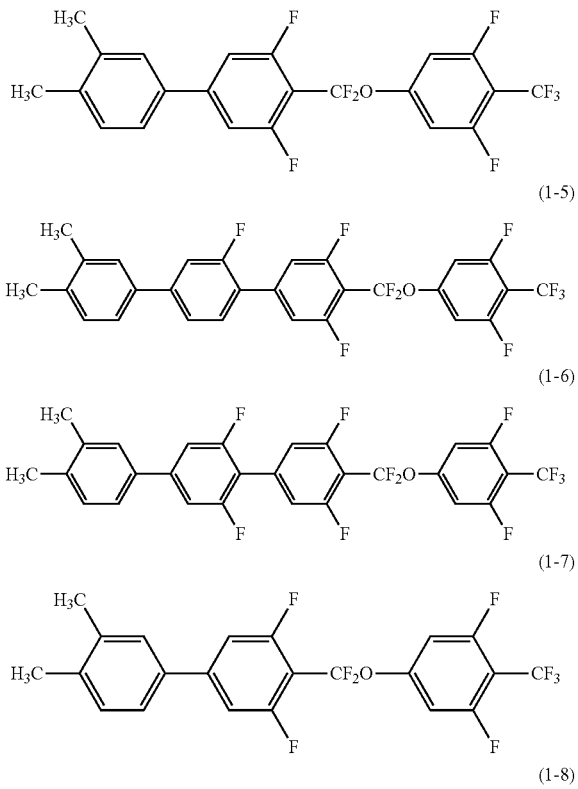
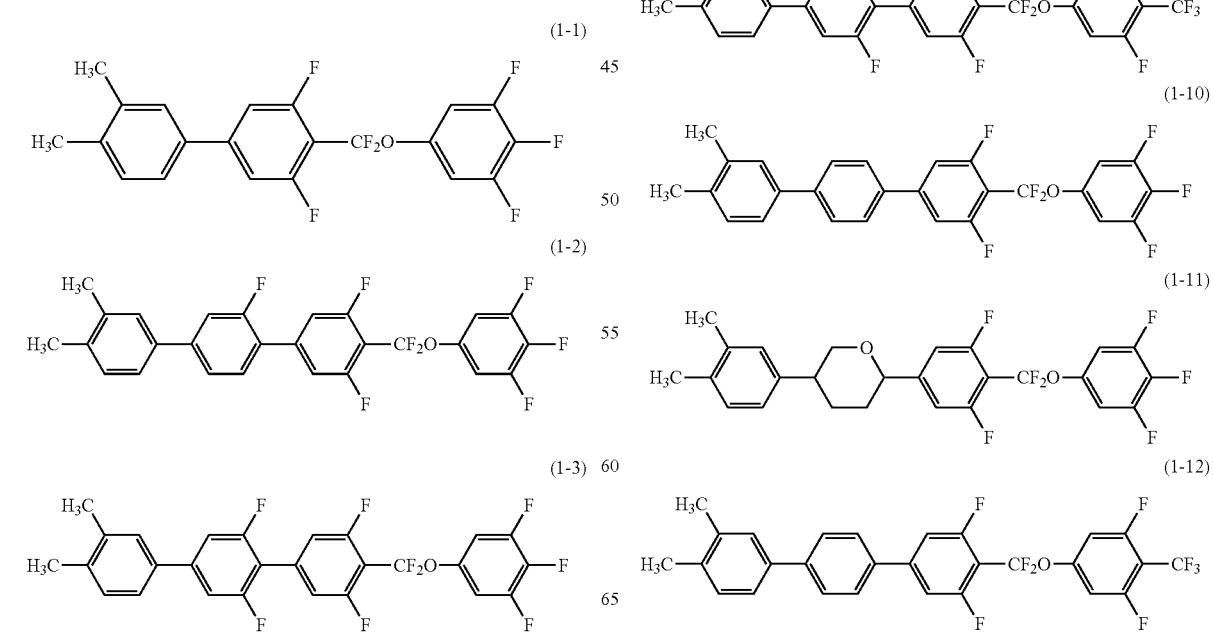

-continued (1-13)
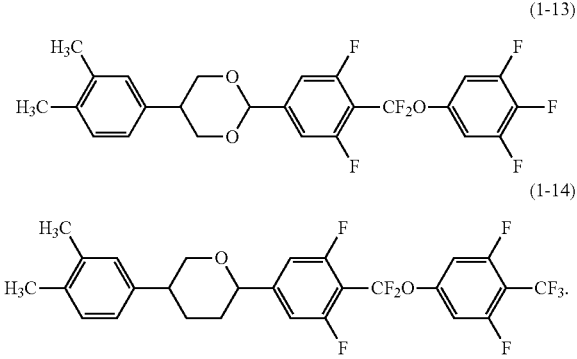

(1-14)

16. The liquid crystal display of claim 14, wherein a content of the compound represented by Chemical Formula 1 is in a range of about 1 wt % to about 30 wt % of the total weight of the liquid crystal composition.

17. The liquid crystal display of claim 14, wherein the liquid crystal composition further comprises one or more of the compound represented by Chemical Formula 2:

[Chemical Formula 2]

wherein, in Chemical Formula 2, $R_1$ and $R_2$ independently indicate C1 to C12 alkyl, C1 to C12 alkoxy, or C2 to C12 alkenyl.

18. The liquid crystal display of claim 17, wherein a content of the compound represented by Chemical Formula 2 is in a range of about 5 wt % to about 60 wt % of the total weight of the liquid crystal composition.

19. The liquid crystal display of claim 14, wherein the liquid crystal composition further comprises one or more of the compound represented by Chemical Formula 3:

[Chemical Formula 3]

wherein each of

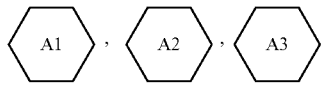

is independently

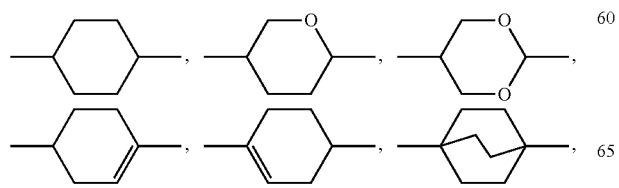

-continued

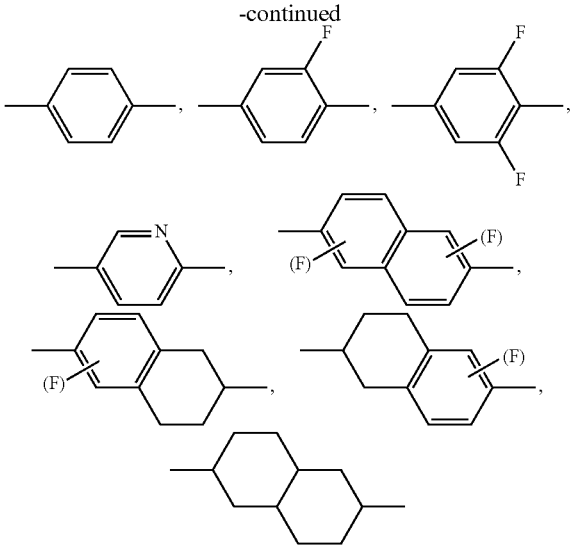

wherein (F) indicates that a fluoro is optionally substituted in place of a hydrogen, and $R_3$ and $R_4$ independently indicate C1 to C12 alkyl, C1 to C12 alkoxy, or C2 to C12 alkenyl.

20. The liquid crystal display of claim 19, wherein a content of the compound represented by Chemical Formula 3 is in a range of about 1 wt % to about 40 wt % of the total weight of the liquid crystal composition.

21. The liquid crystal display of claim 14, wherein the liquid crystal composition further comprises one or more of the compound represented by Chemical Formula 4:

[Chemical Formula 4]

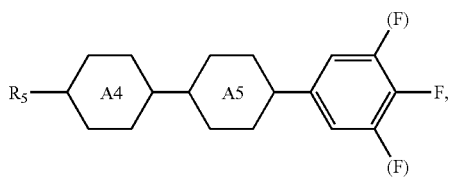

wherein each of

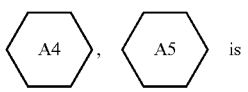

is

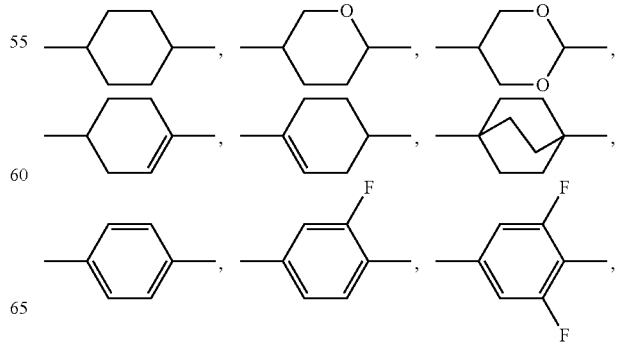

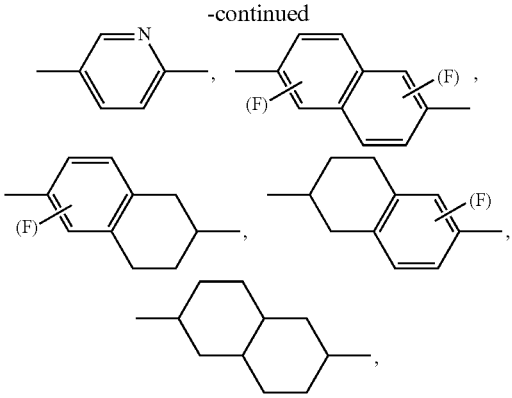

wherein $R_5$ indicates C1 to C12 alkyl, C1 to C12 alkoxy, or C2 to C12 alkenyl, and (F) indicates that a fluoro is substituted or unsubstituted.

22. The liquid crystal display of claim 21, wherein a content of the compound represented by Chemical Formula 4 is in a range of about 1 wt % to about 40 wt % of the total weight of the liquid crystal composition.

23. The liquid crystal display of claim 14, wherein the liquid crystal composition further comprises one or more of the compound represented by Chemical Formula 5:

[Chemical Formula 5]

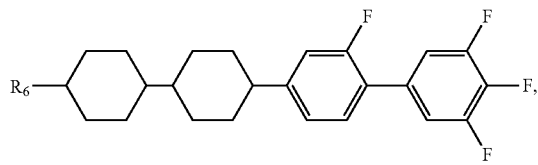

wherein $R_6$ indicates C1 to C12 alkyl, C1 to C12 alkoxy, or C2 to C12 alkenyl.

24. The liquid crystal display of claim 23, wherein a content of the compound represented by Chemical Formula 5 is in a range of about 1 wt % to about 15 wt % of the total weight of the liquid crystal composition.

\* \* \* \* \*